United States Patent
Monteleone

(10) Patent No.: US 10,337,004 B2
(45) Date of Patent: Jul. 2, 2019

(54) METHODS AND COMPOSITIONS FOR TREATING A SUBJECT WITH A SMAD7 ANTISENSE OLIGONUCLEOTIDE

(71) Applicant: Nogra Pharma Limited, Dublin (IE)

(72) Inventor: Giovanni Monteleone, Grottaferrata (IT)

(73) Assignee: Nogra Pharma Limited, Dublin (IE)

( * ) Notice: Subject to any disclaimer, the term of this patent is extended or adjusted under 35 U.S.C. 154(b) by 0 days.

(21) Appl. No.: 15/519,468

(22) PCT Filed: Oct. 16, 2015

(86) PCT No.: PCT/EP2015/074066
§ 371 (c)(1),
(2) Date: Apr. 14, 2017

(87) PCT Pub. No.: WO2016/059239
PCT Pub. Date: Apr. 21, 2016

(65) Prior Publication Data
US 2017/0240893 A1 Aug. 24, 2017

Related U.S. Application Data

(60) Provisional application No. 62/065,598, filed on Oct. 17, 2014.

(51) Int. Cl.
*C07H 21/04* (2006.01)
*C12N 15/113* (2010.01)
*C12Q 1/6883* (2018.01)

(52) U.S. Cl.
CPC .......... *C12N 15/113* (2013.01); *C12Q 1/6883* (2013.01); *C12N 2310/11* (2013.01); *C12N 2310/111* (2013.01); *C12N 2310/315* (2013.01); *C12N 2310/322* (2013.01); *C12N 2310/3341* (2013.01); *C12N 2320/34* (2013.01); *C12N 2320/35* (2013.01); *C12Q 2600/156* (2013.01)

(58) Field of Classification Search
CPC .................................................. C12N 15/111
See application file for complete search history.

(56) References Cited

U.S. PATENT DOCUMENTS

| | | | |
|---|---|---|---|
| 7,700,572 B2 | 4/2010 | Steinbrecher et al. |
| 7,700,757 B2 | 4/2010 | Monteleone |
| 7,807,818 B2 | 10/2010 | Monteleone |
| 8,106,182 B2 | 1/2012 | Monteleone |
| 8,648,186 B2 | 2/2014 | Monteleone |
| 8,907,078 B2 | 12/2014 | Monteleone |
| 8,912,154 B2 | 12/2014 | Baroni et al. |
| 9,006,418 B2 | 4/2015 | Monteleone |
| 9,096,854 B1 | 8/2015 | Monteleone |
| 9,279,126 B2 | 3/2016 | Monteleone |
| 9,314,434 B2 | 4/2016 | Baroni et al. |
| 9,382,541 B2 | 7/2016 | Monteleone |
| 9,499,819 B2 | 11/2016 | Baroni et al. |
| 9,518,264 B2 | 12/2016 | Monteleone |
| 9,605,264 B2 | 3/2017 | Monteleone |
| 9,791,442 B2 | 10/2017 | Monteleone et al. |
| 9,951,334 B2 | 4/2018 | Monteleone |
| 9,982,264 B2 | 5/2018 | Baroni et al. |
| 10,006,029 B2 | 6/2018 | Monteleone et al. |
| 10,036,022 B2 | 7/2018 | Monteleone |
| 10,081,809 B2 | 9/2018 | Monteleone et al. |
| 2005/0119203 A1 | 6/2005 | Steinbrecher et al. |
| 2007/0042985 A1 | 2/2007 | Monteleone |
| 2007/0167385 A1 | 7/2007 | Monteleone |
| 2009/0156539 A1 | 6/2009 | Monteleone |
| 2010/0317719 A1 | 12/2010 | Monteleone |
| 2011/0207795 A1 | 8/2011 | Steinbrecher et al. |
| 2012/0015033 A1 | 1/2012 | Baroni et al. |
| 2012/0136043 A1 | 5/2012 | Monteleone |
| 2013/0203839 A1 | 8/2013 | Monteleone |
| 2014/0142163 A1 | 5/2014 | Monteleone |
| 2014/0256788 A1 | 9/2014 | Monteleone |
| 2014/0271860 A1 | 9/2014 | Monteleone et al. |
| 2015/0125523 A1 | 5/2015 | Baroni et al. |
| 2015/0148245 A1 | 5/2015 | Monteleone et al. |
| 2015/0211011 A1 | 7/2015 | Monteleone |
| 2015/0218561 A1 | 8/2015 | Monteleone |
| 2015/0232854 A1 | 8/2015 | Baroni et al. |
| 2015/0315573 A1 | 11/2015 | Monteleone et al. |

(Continued)

FOREIGN PATENT DOCUMENTS

| WO | WO-2003/037368 A2 | 5/2003 |
|---|---|---|
| WO | WO-2004/087920 A2 | 10/2004 |

(Continued)

OTHER PUBLICATIONS

Arican O et al., (2005), 'Serum Levels of TNF-α, INF-γ, IL-6, IL-8, IL-12, IL-17, and IL-18 in Patients with Active Psoriasis and Correlation with Disease Severity,' Mediators Inflamm, 2005(5):273-9.

Best WR et al., (1976), 'Development of Crohn's Disease Activity Index. National Cooperative Crohn's Disease Study,' Gastroenterology, 70(3);439-44.

Database dbSNP [Online], (Updated Oct. 19, 2016), 'Reference SNP (refSNP) Cluster Report: rs144204026,' SMAD7, National Center for Biotechnology Information, U.S. National Library of Medicine, Bethesda, MD (Publ), pp. 1-3 XP-002752629 [downloaded from the internet from <http://www.ncbi.nlm.nih.gov/SNP/snp_ref.cgi?rs=rs144204026> on Jan. 5, 2016].

(Continued)

Primary Examiner — Kimberly Chong
(74) Attorney, Agent, or Firm — Goodwin Procter LLP

(57) ABSTRACT

The present invention relates to treatment of inflammatory bowel disease (e.g., Crohn's disease and ulcerative colitis) using antisense nucleotides that are directed against polymorphic forms (e.g., those containing single nucleotide polymorphisms) of the SMAD7 mRNA. The invention thus relates to treatment methods for subjects having polymorphic forms of SMAD7 and antisense oligonucleotides that specifically target SMAD7 mRNA transcripts containing polymorphisms.

8 Claims, No Drawings

Specification includes a Sequence Listing.

(56) References Cited

U.S. PATENT DOCUMENTS

| | | |
|---|---|---|
| 2015/0337312 A1 | 11/2015 | Monteleone |
| 2016/0177306 A1 | 6/2016 | Monteleone |
| 2016/0222383 A1 | 8/2016 | Baroni et al. |
| 2016/0304876 A1 | 10/2016 | Monteleone |
| 2017/0107520 A1 | 4/2017 | Baroni et al. |
| 2017/0233736 A1 | 8/2017 | Monteleone et al. |
| 2017/0253880 A1 | 9/2017 | Monteleone |
| 2018/0030450 A1 | 2/2018 | Monteleone |
| 2018/0128829 A1 | 5/2018 | Monteleone et al. |
| 2018/0180630 A1 | 6/2018 | Monteleone |

FOREIGN PATENT DOCUMENTS

| | | |
|---|---|---|
| WO | WO-2010/054826 A1 | 5/2010 |
| WO | WO-2013/037970 A1 | 3/2013 |
| WO | WO-2013/158868 A1 | 10/2013 |
| WO | WO-2014/140333 A1 | 9/2014 |
| WO | WO-2015/011694 A2 | 1/2015 |
| WO | WO-2015/169966 A2 | 11/2015 |
| WO | WO-2016/059239 A1 | 4/2016 |
| WO | WO-2016/059243 A2 | 4/2016 |
| WO | WO-2016/105516 A1 | 6/2016 |
| WO | WO-2017/055611 A2 | 4/2017 |
| WO | WO-2017/059225 A1 | 4/2017 |

OTHER PUBLICATIONS

Howell WM et al., (1999), 'Dynamic Allele-Specific Hybridization. A New Method for Scoring Single Nucleotide Polymorphisms,' Nat Biotechnol, 17(1):87-8.

International Search Report for International Application No. PCT/EP2015/074066, dated Jan. 25, 2016 (5 pages).

Mhlanga MM and Malmberg L, (2001), 'Using Molecular Beacons to Detect Single-Nucleotide Polymorphisms with Real-Time PCR,' Methods, 25(4):463-71.

Monteleone G et al., (2001), 'Blocking Smad7 Restores TGF-β1 Signaling in Chronic Inflammatory Bowel Disease,' J Clin Invest,108(4):601-9.

Monteleone G et al., (2012), 'Phase I Clinical Trial of Smad7 Knockdown Using Antisense Oligonucleotide in Patients with Active Crohn's Disease,' Mol Ther, 20(4):870-6.

Monteleone G et al., (2012), 'Role of Smad7 in Inflammatory Bowel Disease,' World J Gastroenterol, 18(40);5664-8.

Monteleone G et al., (2015), 'Mongersen, an Oral SMAD7 Antisense Oligonucleotide, and Crohn's Disease,' N Engl J Med, 372(12):1104-13.

Sutherland LR et al., (1987), '5-Aminosalicylic Acid Enema in the Treatment of Distal Ulcerative Colitis, Proctosigmoiditis, and Proctitis,' Gastroenterology, 92(6):1894-8.

Written Opinion of the International Searching Authority for International Application No. PCT/EP2015/074066, dated Jan. 25, 2016 (6 pages).

METHODS AND COMPOSITIONS FOR TREATING A SUBJECT WITH A SMAD7 ANTISENSE OLIGONUCLEOTIDE

CROSS-REFERENCE TO RELATED APPLICATIONS

This application is a national stage filing under 35 U.S.C. § 371 of International Application No. PCT/EP2015/074066, filed Oct. 16, 2015, which claims the benefit of and priority to U.S. Provisional Application No. 62/065,598, filed Oct. 17, 2014, the entire contents of each of which are herein incorporated by reference for all purposes.

BACKGROUND

Inflammatory bowel disease (IBD) is a chronic inflammatory disorder of the gastrointestinal tract suffered by approximately one million patients in the United States. The two most common forms of IBD are Crohn's disease (CD) and ulcerative colitis (UC). Although CD can affect the entire gastrointestinal tract, it primarily affects the ileum (the distal or lower portion of the small intestine) and the large intestine. UC primarily affects the colon and the rectum. Current treatment for both CD and UC include aminosalicylates (e.g., 5-aminosalicylic acid, sulfasalazine, and mesalamine), antibiotics (e.g., ciprofloxacin and metronidazole), corticosteroids (e.g., budesonide or prednisone), immunosuppressants (e.g., azathioprine or methotrexate), and tumor necrosis factor (TNF) antagonists (e.g., infliximab (Remicade®)). Patient response to these therapies varies with disease severity, and it can vary over cycles of active inflammation and remission. Moreover, many of the current therapies for IBD are associated with undesirable side effects.

Although the etiologies of CD and UC are unknown, both are considered inflammatory diseases of the intestinal mucosa. Recent studies have demonstrated that TGF-β1 acts as a potent immunoregulator able to control mucosal intestinal inflammation. TGF-β1 binds a heterodimeric transmembrane serine/threonine kinase receptor containing two subunits, TGF-β1 R1 and TGF-β1 R2. Upon ligand binding, the TGF-β1 R1 receptor is phosphorylated by the constitutively active TGF-β1 R2 receptor and signal is propagated to the nucleus by proteins belonging to the SMAD family. Activated TGF-β1 R1 directly phosphorylates SMAD2 and SMAD3 proteins, which then interact with SMAD4. The complex of SMAD2/SMAD3/SMAD4 translocates to the nucleus and modulates the transcription of certain genes.

Additional studies have demonstrated that another SMAD protein, SMAD7, also plays a role in inflammation. SMAD7, an intracellular protein, has been shown to interfere with binding of SMAD2/SMAD3 to the TGF-β1 R1, preventing phosphorylation and activation of these proteins. Further, increased expression of SMAD7 protein is associated with an inhibition of TGF-β1 mediated-signaling. Mucosal samples from IBD patients are characterized by high levels of SMAD7 and reduced levels of phosphorylated-SMAD3 indicating that TGF-β1-mediated signaling is compromised in these patients.

Recent studies have focused on SMAD7 as a target for treating patients suffering from IBD. Such therapies include anti-SMAD7 antisense therapies.

SUMMARY

The present invention is based on the development of methods for treating patient having inflammatory bowel disease using antisense therapeutics directed against SMAD7 that are tailored to the particular polymorphic form(s) of SMAD7 present in the patient. In a particular example, the presence of a single nucleotide polymorphism (Reference SNP rs144204026) that is present within nucleotides 108-128 of the coding sequence of SMAD7, which corresponds to the region of the SMAD7 mRNA targeted by the antisense therapeutic Mongersen, can make it desirable to target this region using a modified form of Mongersen that includes the polymorphism. Accordingly, the present invention features methods for treating subjects having polymorphism(s) in the SMAD7 mRNA sequence using an antisense therapeutic having a sequence specific for (e.g., matches exactly) the polymorphic gene sequence. The invention also features antisense oligonucleotides that include the polymorphic sequence.

Accordingly in a first aspect, the invention features a method for treating or managing inflammatory bowel disease (IBD; e.g., Crohn's disease (CD) or ulcerative colitis (UC)) in a patient having IBD that carries at least one copy of a first polymorphic form of SMAD7 that differs from the consensus SMAD7 nucleotide sequence. The method includes administering to said patient an effective amount of a first SMAD7 antisense oligonucleotide that specifically targets said first polymorphic form of SMAD7. The polymorphic form of SMAD7 may include a single nucleotide polymorphism (SNP) and/or may include a polymorphism listed in Table 1 or in Table 2. The first polymorphic form may include a polymorphism in the region corresponding to nucleic acid positions 108-128 of SEQ ID NO:1 (e.g., an adenosine ("A") or a guanine ("G") at position 114 of SEQ ID NO:1); for example, where the polymorphic form includes the nucleic acid sequence of SEQ ID NO:9 (5'-GCTGCGGAGAGAAGGGGCGAC-3'). In some embodiments, the first polymorphic form may include the nucleic acid sequence of SEQ ID NO:3 (5'-GCTGCGGGGAGAAGGGGCGAC-3'). In particular embodiments, the first SMAD7 antisense oligonucleotide includes the nucleotide sequence of SEQ ID NO:11 (5'-GTCGCCCCTTCTCTCCGCAGC-3'), for example, where the first SMAD7 antisense oligonucleotide is an antisense oligonucleotide phosphorothioate including the following sequence: 5'-GTXGCCCCTTCTCTCXGCAGC-3' (SEQ ID NO:13) where X is 5-methyl-2'-deoxycytidine and where all internucleotide linkages are phosphorothioate linkages. In other particular embodiments, the first SMAD7 antisense oligonucleotide includes the nucleotide sequence of SEQ ID NO:5 (5'-GTCGCCCCTTCTCCCCGCAGC-3'), for example, where the first SMAD7 antisense oligonucleotide is an antisense oligonucleotide phosphorothioate including the following sequence: 5'-GTXGCCCCTTCTCCCXGCAGC-3' (SEQ ID NO:7) where X is 5-methyl-2'-deoxycytidine and where all internucleotide linkages are phosphorothioate linkages.

In another aspect, the invention features a method for treating or managing IBD (e.g., CD or UC) in a patient having IBD. The method includes (a) analyzing the presence or absence of one or more SMAD7 polymorphic forms in the patient; and (b) administering one or more SMAD7 antisense oligonucleotides to the patient, based on the presence or absence of said polymorphic forms, where: (i) if a first SMAD7 polymorphic form (e.g., the wild type form) is present in the patient, then administering to the patient a first SMAD7 antisense oligonucleotide targeting the first SMAD7 polymorphic form; or (ii) if a second SMAD7 polymorphic form is present in the patient, then administering to the patient a second SMAD7 antisense oligonucleotide targeting the second SMAD7 polymorphic form; or (iii) if the first and the second SMAD7 polymorphic forms are present in the patient, then administering to the patient one or both of the first and the second SMAD7 antisense oligonucleotide targeting the first and the second SMAD7 polymorphic forms. The polymorphism can include an SNP and/or can include a polymorphism listed in Table 1 or in Table 2. The first polymorphism can occur in the region corresponding to nucleic acid positions 108-128 of SEQ ID NO:1 (e.g., where the first SMAD7 polymorphic variant includes a guanine ("G") at position 114 of SEQ ID NO:1). The second SMAD7 polymorphic form can include an adenine ("A") at position 114 of SEQ ID NO:1. In certain embodiments, the first SMAD7 polymorphic form includes the nucleic acid sequence of SEQ ID NO:3 (5'-GCTGCGG GGAGAAGGGGCGAC-3'). In particular embodiments, the first SMAD7 antisense oligonucleotide includes the nucleotide sequence of SEQ ID NO:5 (5'-GTCGCCCCTTCTC CCCGCAGC-3'), for example, where the first SMAD7 antisense oligonucleotide is an antisense oligonucleotide phosphorothioate including the following sequence: 5'-GTXGCCCCTTCTCCCXGCAGC-3' (SEQ ID NO:7) where X is 5-methyl-2'-deoxycytidine and where all internucleotide linkages are phosphorothioate linkages. In certain embodiments, the second SMAD7 polymorphic form includes the nucleic acid sequence of SEQ ID NO:9 (5'-GCTGCGGAGAGAAGGGGCGAC-3'). In particular embodiments, the second SMAD7 antisense oligonucleotide includes the nucleotide sequence of SEQ ID NO:11 (5'-GTCGCCCCTTCTCTCCGCAGC-3'), for example, where the second SMAD7 antisense oligonucleotide is an antisense oligonucleotide phosphorothioate including the sequence 5'-GTXGCCCCTTCTCTCXGCAGC-3' (SEQ ID NO:13) where X is 5-methyl-2'-deoxycytidine and where all internucleotide linkages are phosphorothioate linkages. The presence or absence of the one or more SMAD7 polymorphic forms may be analyzed by DNA sequencing, by gene-expression profiling, using next-generation sequencing, or using gene expression microarray analysis. The presence or absence of the one or more SMAD7 polymorphic forms may be analyzed in a sample (e.g., a liquid, a biopsy sample, or a tissue sample) obtained from the patient.

In any of the above aspects, the first and/or the second SMAD7 antisense oligonucleotide may be administered to the patient having IBD at a dose of between 10 mg/day to about 300 mg/day, for example, at a dose of about 10 mg/day, 20 mg/day, about 30 mg/day, about 40 mg/day, about 50 mg/day, about 60 mg/day, about 70 mg/day, about 80 mg/day, about 90 mg/day, about 100 mg/day, about 110 mg/day, about 120 mg/day, about 130 mg/day, about 140 mg/day, about 150 mg/day, about 160 mg/day, about 170 mg/day, about 180 mg/day, about 190 mg/day, about 200 mg/day, about 210 mg/day, about 220 mg/day, about 230 mg/day, about 240 mg/day, about 250 mg/day, about 260 mg/day, about 270 mg/day, about 280 mg/day, about 290 mg/day, or about 300 mg/day. In particular embodiments, the first and/or the second SMAD7 antisense oligonucleotide is administered at a dose of about 40 mg/day, about 80 mg/day, or about 160 mg/day.

In another aspect, the invention features: (a) a SMAD7 antisense oligonucleotide that includes the nucleotide sequence of SEQ ID NO:11, (b) a SMAD7 antisense oligonucleotide that includes the nucleotide sequence of SEQ ID NO:13, where X is a nucleotide including 5-methyl-2'-deoxycytidine and where all internucleotide linkages are phosphorothioate linkages; or (c) a SMAD7 antisense oligonucleotide that includes the nucleotide sequence of SEQ ID NO:13, where X is 5-methyl-2'-deoxycytidine, or a complement thereof. The SMAD7 antisense oligonucleotide may include at least one internucleotide linkage that is a phosphorothioate linkage, e.g., where all internucleotide linkages are phosphorothioate linkages. The oligonucleotide may have 2'-deoxyribonucleotides replaced by corresponding ribonucleotides. The invention also features a pharmaceutical composition (e.g., a composition suitable for oral administration) including the SMAD7 antisense oligonucleotide and a pharmaceutically acceptable adjuvant and/or excipient.

In another aspect, the invention features a method of treating IBD (e.g., CD or UC), including administering (e.g., orally) to a patient in need thereof an effective amount of the SMAD7 antisense oligonucleotide of the previous aspect, where the SMAD7 antisense oligonucleotide is effective to treat IBD.

Antisense oligonucleotides are short synthetic oligonucleotide sequences that are complementary to a messenger RNA (mRNA) transcribed from a target gene (e.g., a polymorphic form of SMAD7). Antisense oligonucleotide sequences hybridize to the mRNA and produce a double-strand hybrid that can lead to the activation of ubiquitary catalytic enzymes, such as RNase H, which degrades DNA/RNA hybrid strands, thus preventing protein translation. Without being bound by theory, an antisense oligonucleotide provided herein can hybridize to its target sequence as RNA or DNA. Thus, even if a DNA sequence is provided as target, the corresponding RNA sequence (including uracil instead of thymine) is included.

In another aspect, the present invention provides an antisense therapeutic directed against SMAD7 as described above for use as a medicament. The present invention provides an antisense therapeutic directed against SMAD7 which has been tailored to the particular polymorphic form(s) of SMAD7 present in the patient, for use in a method for treating patient having inflammatory bowel disease. In a particular example, the presence of a single nucleotide polymorphism (Reference SNP rs144204026) that is present within nucleotides 108-128 of the coding sequence of SMAD7, which corresponds to the region of the SMAD7 mRNA targeted by the antisense therapeutic Mongersen, can make it desirable to target this region using a modified form of Mongersen that includes the polymorphism. The present invention also provides an antisense therapeutic for use in a method for treating subjects having polymorphism(s) in the SMAD7 mRNA sequence, said antisense therapeutic having a sequence specific for (e.g., matches exactly) the polymorphic gene sequence.

The present invention also provides a SMAD7 antisense oligonucleotide for use in a method for treating or managing inflammatory bowel disease (IBD; e.g., Crohn's disease (CD) or ulcerative colitis (UC)) in a patient having IBD that carries at least one copy of a first polymorphic form of SMAD7 that differs from the consensus SMAD7 nucleotide sequence. Preferably, the SMAD7 antisense oligonucleotide specifically targets said first polymorphic form of SMAD7. The polymorphic form of SMAD7 may include a single nucleotide polymorphism (SNP) and/or may include a polymorphism listed in Table 1 or in Table 2 or as listed in paragraph [0007].

The present invention also provides a SMAD7 antisense oligonucleotide for use in a method of treating or managing inflammatory bowel disease (IBD; e.g., Crohn's disease (CD) or ulcerative colitis (UC)) in a patient having IBD. Preferably the method (a) analyzing the presence or absence of one or more SMAD7 polymorphic forms in the patient;

and (b) administering one or more SMAD7 antisense oligonucleotides to the patient, based on the presence or absence of said polymorphic forms, where: (i) if a first SMAD7 polymorphic form (e.g., the wild type form) is present in the patient, then administering to the patient a first SMAD7 antisense oligonucleotide targeting the first SMAD7 polymorphic form; or (ii) if a second SMAD7 polymorphic form is present in the patient, then administering to the patient a second SMAD7 antisense oligonucleotide targeting the second SMAD7 polymorphic form; or (iii) if the first and the second SMAD7 polymorphic forms are present in the patient, then administering to the patient one or both of the first and the second SMAD7 antisense oligonucleotide targeting the first and the second SMAD7 polymorphic forms. The polymorphism can include an SNP and/or can include a polymorphism listed in Table 1 or in Table 2 or as listed in paragraph [0008].

In another aspect, the invention provides an effective amount of the SMAD7 antisense oligonucleotide as described above for use in a method of treating IBD (e.g., CD or UC), wherein said method includes administering (e.g., orally) to a patient in need thereof an effective amount of the SMAD7 antisense oligonucleotide, where the SMAD7 antisense oligonucleotide is effective to treat IBD.

An antisense oligonucleotide that "specifically targets" a polymorphic form of a gene that differs from a consensus sequence includes a nucleotide sequence with a substitution, relative to the gene or transcript consensus sequence, that increases hybridization of the antisense oligonucleotide to the polymorphic form, as compared to the consensus sequence. For example, a polymorphic form that includes a guanosine to adenine (G→A) change in the target sequence would be specifically targeted by an antisense oligonucleotide containing a cytosine to thymine (C→T) substitution at the corresponding position in the oligonucleotide.

The "consensus" SMAD7 nucleotide sequence means the RNA sequence or DNA sequences associated with the "wild-type" sequence of a gene described in the reference databases. For example, consensus sequences for SMAD7 can be found under Accession numbers NM_005904.3, NM_001190821.1, NM_001190822.1, and NM_001190823.1, which are reference transcripts for human SMAD7 in the National Center for Biotechnology Information (NCBI) database.

By "treating" is meant reducing at least one symptom associated with the disease or condition being treated.

The terms "manage," "management," "managing" and the like are used herein to generally mean controlling the severity or manifestation of symptoms of a disease, or the means of treating the disease. Generally, management is used to obtain a desired pharmacological and/or physiological effect. The effect may be therapeutic in terms of partially or completely curing a disease and/or adverse effect attributed to the disease or ensuring that a particular symptom or manifestation of the disease does not occur or reoccur in a patient or does not rise to an undesirable or intolerable level in a patient. The term "management" as used herein covers any management of a disease in a mammal, particularly a human, and includes: (a) inhibiting the disease, i.e., preventing the disease from increasing in severity or scope; (b) relieving the disease, i.e., causing partial or complete amelioration of the disease; or (c) preventing relapse of the disease, e.g., preventing the disease from returning to an active state following previous successful treatment of symptoms of the disease or treatment of the disease. "Management" as used herein may also be used with reference to administration of a specific treatment for the disease, for example, a SMAD7 antisense oligonucleotide.

A "subject" or "patient" as described herein, refers to any animal at risk for, suffering from or diagnosed for IBD, including, but not limited to, mammals, primates, and humans. In certain embodiments, the subject may be a non-human mammal such as, for example, a cat, a dog, or a horse. In a preferred embodiment, the subject is a human subject. A subject may be an individual diagnosed with a high risk of developing IBD, someone who has been diagnosed with IBD, someone who previously suffered from IBD, or an individual evaluated for symptoms or indications of IBD, for example, a high CDAI index score.

"A patient with IBD," as used herein, refers to a patient suffering from any of the symptoms or manifestations of IBD, a patient who may suffer from any of the symptoms or manifestations of IBD, or any patient who might benefit from a method of the invention for treating or evaluating treatment for IBD. A patient in need may include a patient who is diagnosed with a risk of developing IBD, a patient who has suffered from IBD in the past, or a patient who has previously been treated for IBD. Of particular relevance are individuals that suffer from IBD associated with increased levels of CRP, TNFα, and/or IL8 expression. In some embodiments, the patient with IBD is a Crohn's disease (CD) patient. In some embodiments, the patient with IBD is an ulcerative colitis (UC) patient.

As used herein, "Crohn's Disease Activity Index" or "CDAI" refers to a measurement or index used to assess the progress of patients suffering from CD as described by Best et al., Gastroenterology, 70:439-44 (1976). CDAI scores of 150 or below are generally associated with inactive disease and are indicative of better prognosis than higher scores. Values above 150 are generally associated with active disease and values above 450 are associated with extremely severe disease. CDAI scores may be used to determine how well a patient is responding to therapy and may be used to identify patients in remission. In certain embodiments, a benchmark clinical response means that the subject displays a decrease in CDAI score by at least 100 points. In a clinical trial, a CDAI score of 150 or below is generally associated with remission.

As used herein, "Ulcerative Colitis Disease Activity Index" or "UCDAI" refers to a measurement or index used to assess the progress of patients suffering from UC as described by Sutherland et al., Gastroenterology, 92:1894-98 (1987). The UCDAI is a series of qualifiers about the symptoms of UC including stool frequency, rectal bleeding, the appearance of the colon lining, and a physician's rating of disease activity. Each of these qualifiers is given a number from 0 to 3, with 3 being the highest disease activity. In a clinical trial, remission is often defined as a UCDAI score of 1 or less, and improvement is a reduction of 3 or more points from the score at the beginning of the trial. UCDAI may be used in clinical trials to determine how well a patient is responding to therapy and may be used to identify patients in remission. Other commonly used indices for measuring disease severity in UC patients include the Truelove and Witts Index, the St. Mark's Index, the Simple Clinical Colitis Activity Index (SCCAI), the Lichtiger Index, the Ulcerative Colitis Symptom Score (UCSS), and the Mayo Clinic Score.

As used herein, "SMAD7" (also known as CRCS3, FLJ16482, MADH7, MADH8, MAD (mothers against decapentaplegic, *Drosophila*) homolog 7, MAD homolog 8, SMAD, mothers against DPP homolog 7, mothers against DPP homolog 8) means the human protein or any of the mRNA transcripts encoded by the gene identified by Entrez GeneID No. 4092 and allelic variants thereof.

As used herein, "CRP" (also known as C-reactive protein, pentraxin-related; Pentraxin; and PTX1) means the human protein or any of the mRNA transcripts encoded by the gene identified by Entrez GeneID No. 1401 and allelic variants thereof.

As used herein, "IL8" (also known as Interleukin-8 (IL-8); Tumor Necrosis Factor-Induced Gene 1; NAF; Granulocyte Chemotactic Protein 1 (GCP1); LECT; LUCT; Protein 3-10C; Beta-Thromboglobulin-Like Protein; Neutrophil-Activating Peptide 1; Neutrophil-Activating Protein 1 (NAP1; NAP-1); Emoctakin; GCP-1; LYNAP; Lymphocyte Derived Neutrophil Activating Peptide; Lung Giant Cell Carcinoma-Derived Chemotactic Protein; Small Inducible Cytokine Subfamily B, Member 8; Beta Endothelial Cell-Derived Neutrophil Activating Peptide; Monocyte-Derived Neutrophil Chemotactic Factor (MDNCF); Monocyte-Derived Neutrophil-Activating Peptide (MONAP); Alveolar Macrophage Chemotactic Factor I; C-X-C Motif Chemokine 8; and Chemokine (C-X-C Motif) Ligand 8 (CXCL8)) means the human protein or any of the mRNA transcripts encoded by the gene identified by Entrez GeneID No. 3576 and allelic variants thereof.

As used herein, "TNFα" (also known as Tumor Necrosis Factor, DIF, Tumor Necrosis Factor Ligand Superfamily Member 2 (TNFSF2), APC1 Protein, cachectin, Tumor Necrosis Factor A (TNFA), Tumor Necrosis Factor-α (TNF-α), and Tumor Necrosis Factor-alpha (TNF-alpha)) means the human protein or any of the mRNA transcripts encoded by the gene identified by Entrez GeneID No. 7124 and allelic variants thereof.

DETAILED DESCRIPTION

The present invention relates to methods for treating inflammatory bowel disease (IBD; e.g., Crohn's disease and ulcerative colitis) in patients that have a polymorphic form of the SMAD7 gene. This approach uses antisense oligonucleotides specifically designed to target the SMAD7 transcripts containing the polymorphism, thus allowing for targeting those patient with greater efficacy. This approach is explained in greater detail below.

SMAD7 Polymorphic Variants

The methods and antisense oligonucleotides of the invention can target any SMAD7 polymorphism. In general, the targeted polymorphisms are present in the mRNA sequence. SNPs found in the SMAD7 mRNA include those listed in Table 1. Although the sequences of the SMAD7 SNPs in Table 1 are shown as DNA sequences, the skilled artisan will appreciate that hybridization in a cell can occur with RNA, which contains uracil (U) instead of thymine (T). SNPs within the SMAD7 coding sequence are listed in Table 2.

TABLE 1

| mRNA Position | dbSNP rs# Cluster ID | Function | db SNP allele | Protein Residue | Codon Position | Amino Acid Position |
|---|---|---|---|---|---|---|
| 3044 | rs184940583 | UTR-3 contig reference | G A | | | |
| 2795 | rs16950112 | UTR-3 contig reference | C A | | | |
| 2721 | rs16950113 | UTR-3 contig reference | G A | | | |
| 2650 | rs142341429 | UTR-3 contig reference | A G | | | |
| 2505 | rs190053734 | UTR-3 contig reference | T C | | | |
| 2470 | rs8088297 | UTR-3 contig reference | G T | | | |
| 2434 | rs146277807 | UTR-3 contig reference | A G | | | |
| 2433 | rs112439201 | UTR-3 contig reference | T C | | | |
| 2285 | rs192920849 | UTR-3 contig reference | T C | | | |
| 2179 | rs375444823 | UTR-3 contig reference | A G | | | |
| 2162 | rs138939641 | UTR-3 contig reference | C T | | | |
| 2071 | rs184768687 | UTR-3 contig reference | A G | | | |
| 1940 | rs368597621 | UTR-3 contig reference | T C | | | |
| 1912-1915 | rs145497223 | UTR-3 contig reference | — AGTG | | | |

TABLE 1-continued

| mRNA Position | dbSNP rs# Cluster ID | Function | db SNP allele | Protein Residue | Codon Position | Amino Acid Position |
|---|---|---|---|---|---|---|
| 1886 | rs142857154 | UTR-3 | G | | | |
| | | contig reference | C | | | |
| 1880 | rs150355680 | UTR-3 | A | | | |
| | | contig reference | G | | | |
| 1879 | rs189546111 | UTR-3 | T | | | |
| | | contig reference | C | | | |
| 1872-1873 | rs35564009 | UTR-3 | G | | | |
| | | contig reference | — | | | |
| 1686-1687 | rs370493054 | UTR-3 | T | | | |
| | | contig reference | — | | | |
| 1676 | rs74509535 | UTR-3 | A | | | |
| | | contig reference | G | | | |
| 1611 | rs200839822 | UTR-3 | C | | | |
| | | contig reference | T | | | |
| 1591 | rs181999754 | UTR-3 | A | | | |
| | | contig reference | G | | | |
| 1590 | rs371306207 | UTR-3 | T | | | |
| | | contig reference | C | | | |
| 1577 | rs374817806 | UTR-3 | A | | | |
| | | contig reference | G | | | |
| 1573 | rs369794757 | UTR-3 | A | | | |
| | | contig reference | G | | | |
| 1572 | rs201583721 | UTR-3 | T | | | |
| | | contig reference | C | | | |
| 1561-1562 | rs35799462 | frame shift | C | Pro [P] | 2 | 426 |
| | | contig reference | — | Arg [R] | 2 | 426 |
| 1559-1560 | rs137881631 | frame shift | CCCCCC | [PP] | 3 | 424 |
| | | contig reference | — | | | |
| 1558 | rs76172388 | missense | C | Thr [T] | 2 | 424 |
| | | contig reference | A | Asn [N] | 2 | 424 |
| 1557 | rs79500688 | missense | C | His [H] | 1 | 424 |
| | | contig reference | A | Asn [N] | 1 | 424 |
| 1535 | rs143029140 | synonymous | C | Pro [P] | 3 | 416 |
| | | contig reference | G | Pro [P] | 3 | 416 |
| 1509 | rs200991750 | missense | C | Pro [P] | 1 | 408 |
| | | contig reference | A | Thr [T] | 1 | 408 |
| 1499 | rs1052572 | synonymous | T | Gly [G] | 3 | 404 |
| | | contig reference | C | Gly [G] | 3 | 404 |
| 1493 | rs3809923 | synonymous | G | Gly [G] | 3 | 402 |
| | | contig reference | C | Gly [G] | 3 | 402 |
| 1492 | rs185241768 | missense | T | Val [V] | 2 | 402 |
| | | contig reference | G | Gly [G] | 2 | 402 |
| 1469 | rs141213977 | synonymous | T | Thr [T] | 3 | 394 |
| | | contig reference | C | Thr [T] | 3 | 394 |
| 1463 | rs200233784 | synonymous | T | Gly [G] | 3 | 392 |
| | | contig reference | C | Gly [G] | 3 | 392 |
| 1460 | rs34151545 | synonymous | C | Thr [T] | 3 | 391 |
| | | contig reference | G | Thr [T] | 3 | 391 |
| 1430 | rs373794913 | synonymous | C | Asn [N] | 3 | 381 |
| | | contig reference | T | Asn [N] | 3 | 381 |

TABLE 1-continued

| mRNA Position | dbSNP rs# Cluster ID | Function | db SNP allele | Protein Residue | Codon Position | Amino Acid Position |
|---|---|---|---|---|---|---|
| 1400 | rs138059462 | synonymous | T | Tyr [Y] | 3 | 371 |
| | | contig reference | C | Tyr [Y] | 3 | 371 |
| 1394 | rs199654760 | synonymous | T | Phe [F] | 3 | 369 |
| | | contig reference | C | Phe [F] | 3 | 369 |
| 1373 | rs149492644 | synonymous | T | Pro [P] | 3 | 362 |
| | | contig reference | C | Pro [P] | 3 | 362 |
| 1337 | rs189328316 | synonymous | A | Pro [P] | 3 | 350 |
| | | contig reference | G | Pro [P] | 3 | 350 |
| 1319 | rs143946125 | synonymous | T | Ser [S] | 3 | 344 |
| | | contig reference | C | Ser [S] | 3 | 344 |
| 1260 | rs146041673 | missense | T | Trp [W] | 1 | 325 |
| | | contig reference | C | Arg [R] | 1 | 325 |
| 1244 | rs201042785 | synonymous | T | Cys [C] | 3 | 319 |
| | | contig reference | C | Cys [C] | 3 | 319 |
| 1240 | rs267605193 | missense | A | Asp [D] | 2 | 318 |
| | | contig reference | G | Gly [G] | 2 | 318 |
| 1229 | rs139969232 | synonymous | A | Arg [R] | 3 | 314 |
| | | contig reference | G | Arg [R] | 3 | 314 |
| 1196 | rs144238958 | synonymous | A | Ser [S] | 3 | 303 |
| | | contig reference | G | Ser [S] | 3 | 303 |
| 1190 | rs376439212 | synonymous | T | Leu [L] | 3 | 301 |
| | | contig reference | C | Leu [L] | 3 | 301 |
| 1181 | rs3809922 | synonymous | T | Leu [L] | 3 | 298 |
| | | contig reference | C | Leu [L] | 3 | 298 |
| 1133 | rs142361633 | synonymous | T | Pro [P] | 3 | 282 |
| | | contig reference | C | Pro [P] | 3 | 282 |
| 1126 | rs369444426 | missense | G | Arg [R] | 2 | 280 |
| | | contig reference | A | Gln [Q] | 2 | 280 |
| 1124 | rs139836741 | synonymous | G | Val [V] | 3 | 279 |
| | | contig reference | C | Val [V] | 3 | 279 |
| 1100 | rs373171169 | synonymous | A | Thr [T] | 3 | 271 |
| | | contig reference | G | Thr [T] | 3 | 271 |
| 1099 | rs147899611 | missense | T | Met [M] | 2 | 271 |
| | | contig reference | C | Thr [T] | 2 | 271 |
| 1059 | rs201671248 | synonymous | A | Arg [R] | 1 | 258 |
| | | contig reference | C | Arg [R] | 1 | 258 |
| 1054 | rs376228389 | missense | A | Glu [E] | 2 | 256 |
| | | contig reference | G | Gly [G] | 2 | 256 |
| 1001 | rs376292728 | synonymous | A | Thr [T] | 3 | 238 |
| | | contig reference | G | Thr [T] | 3 | 238 |
| 984 | rs141795046 | missense | A | Thr [T] | 1 | 233 |
| | | contig reference | G | Ala [A] | 1 | 233 |
| 983 | rs145552668 | synonymous | T | Ser [S] | 3 | 232 |
| | | contig reference | C | Ser [S] | 3 | 232 |
| 953-954 | rs34000389 | frame shift | G | Gly [G] | 3 | 223 |
| | | contig reference | — | Ala [A] | 3 | 223 |
| 951 | rs147707423 | missense | G | Ala [A] | 1 | 222 |
| | | contig reference | A | Thr [T] | 1 | 222 |
| 932 | rs201983335 | synonymous | A | Pro [P] | 3 | 215 |
| | | contig reference | G | Pro [P] | 3 | 215 |

TABLE 1-continued

| mRNA Position | dbSNP rs# Cluster ID | Function | db SNP allele | Protein Residue | Codon Position | Amino Acid Position |
|---|---|---|---|---|---|---|
| 911 | rs145686330 | synonymous | A | Pro [P] | 3 | 208 |
| | | synonymous | T | Pro [P] | 3 | 208 |
| | | contig reference | C | Pro [P] | 3 | 208 |
| 909 | rs113899618 | missense | T | Ser [S] | 1 | 208 |
| | | contig reference | C | Pro [P] | 1 | 208 |
| 895 | rs375674516 | missense | G | Gly [G] | 2 | 203 |
| | | contig reference | A | Glu [E] | 2 | 203 |
| 845 | rs368575800 | synonymous | A | Ile [I] | 3 | 186 |
| | | contig reference | C | Ile [I] | 3 | 186 |
| 837 | rs148818548 | missense | A | Arg [R] | 1 | 184 |
| | | contig reference | G | Gly [G] | 1 | 184 |
| 755 | rs372890425 | synonymous | T | Pro [P] | 3 | 156 |
| | | contig reference | C | Pro [P] | 3 | 156 |
| 749 | rs375582985 | synonymous | A | Ser [S] | 3 | 154 |
| | | contig reference | G | Ser [S] | 3 | 154 |
| 731 | rs137930330 | synonymous | A | Gln [Q] | 3 | 148 |
| | | contig reference | G | Gln [Q] | 3 | 148 |
| 701 | rs369145467 | synonymous | A | Pro [P] | 3 | 138 |
| | | contig reference | G | Pro [P] | 3 | 138 |
| 681 | rs373908933 | synonymous | T | Leu [L] | 1 | 132 |
| | | contig reference | C | Leu [L] | 1 | 132 |
| 434 | rs368427729 | synonymous | A | Gly [G] | 3 | 49 |
| | | contig reference | G | Gly [G] | 3 | 49 |
| 402 | rs144204026 | missense | A | Arg [R] | 1 | 39 |
| | | contig reference | G | Gly [G] | 1 | 39 |
| 277 | rs374325868 | UTR-5 | T | | | |
| | | contig reference | C | | | |
| 258 | rs74507050 | UTR-5 | G | | | |
| | | contig reference | A | | | |

TABLE 2

| | | | | | | |
|---|---|---|---|---|---|---|
| 1561-1562 | rs35799462 | frame shift | C | Pro [P] | 2 | 426 |
| | | contig reference | — | Arg [R] | 2 | 426 |
| 1559-1560 | rs137881631 | frame shift | CCCCCC | [PP] | 3 | 424 |
| | | contig reference | — | | | |
| 1558 | rs76172388 | missense | C | Thr [T] | 2 | 424 |
| | | contig reference | A | Asn [N] | 2 | 424 |
| 1557 | rs79500688 | missense | C | His [H] | 1 | 424 |
| | | contig reference | A | Asn [N] | 1 | 424 |
| 1535 | rs143029140 | synonymous | C | Pro [P] | 3 | 416 |
| | | contig reference | G | Pro [P] | 3 | 416 |
| 1509 | rs200991750 | missense | C | Pro [P] | 1 | 408 |
| | | contig reference | A | Thr [T] | 1 | 408 |
| 1499 | rs1052572 | synonymous | T | Gly [G] | 3 | 404 |
| | | contig reference | C | Gly [G] | 3 | 404 |
| 1493 | rs3809923 | synonymous | G | Gly [G] | 3 | 402 |
| | | contig reference | C | Gly [G] | 3 | 402 |
| 1492 | rs185241768 | missense | T | Val [V] | 2 | 402 |
| | | contig reference | G | Gly [G] | 2 | 402 |

TABLE 2-continued

| | | | | | | |
|---|---|---|---|---|---|---|
| 1469 | rs141213977 | synonymous | T | Thr [T] | 3 | 394 |
| | | contig reference | C | Thr [T] | 3 | 394 |
| 1463 | rs200233784 | synonymous | T | Gly [G] | 3 | 392 |
| | | contig reference | C | Gly [G] | 3 | 392 |
| 1460 | rs34151545 | synonymous | C | Thr [T] | 3 | 391 |
| | | contig reference | G | Thr [T] | 3 | 391 |
| 1430 | rs373794913 | synonymous | C | Asn [N] | 3 | 381 |
| | | contig reference | T | Asn [N] | 3 | 381 |
| 1400 | rs138059462 | synonymous | T | Tyr [Y] | 3 | 371 |
| | | contig reference | C | Tyr [Y] | 3 | 371 |
| 1394 | rs199654760 | synonymous | T | Phe [F] | 3 | 369 |
| | | contig reference | C | Phe [F] | 3 | 369 |
| 1373 | rs149492644 | synonymous | T | Pro [P] | 3 | 362 |
| | | contig reference | C | Pro [P] | 3 | 362 |
| 1337 | rs189328316 | synonymous | A | Pro [P] | 3 | 350 |
| | | contig reference | G | Pro [P] | 3 | 350 |
| 1319 | rs143946125 | synonymous | T | Ser [S] | 3 | 344 |
| | | contig reference | C | Ser [S] | 3 | 344 |
| 1260 | rs146041673 | missense | T | Trp [W] | 1 | 325 |
| | | contig reference | C | Arg [R] | 1 | 325 |
| 1244 | rs201042785 | synonymous | T | Cys [C] | 3 | 319 |
| | | contig reference | C | Cys [C] | 3 | 319 |
| 1240 | rs267605193 | missense | A | Asp [D] | 2 | 318 |
| | | contig reference | G | Gly [G] | 2 | 318 |
| 1229 | rs139969232 | synonymous | A | Arg [R] | 3 | 314 |
| | | contig reference | G | Arg [R] | 3 | 314 |
| 1196 | rs144238958 | synonymous | A | Ser [S] | 3 | 303 |
| | | contig reference | G | Ser [S] | 3 | 303 |
| 1190 | rs376439212 | synonymous | T | Leu [L] | 3 | 301 |
| | | contig reference | C | Leu [L] | 3 | 301 |
| 1181 | rs3809922 | synonymous | T | Leu [L] | 3 | 298 |
| | | contig reference | C | Leu [L] | 3 | 298 |
| 1133 | rs142361633 | synonymous | T | Pro [P] | 3 | 282 |
| | | contig reference | C | Pro [P] | 3 | 282 |
| 1126 | rs369444426 | missense | G | Arg [R] | 2 | 280 |
| | | contig reference | A | Gln [Q] | 2 | 280 |
| 1124 | rs139836741 | synonymous | G | Val [V] | 3 | 279 |
| | | contig reference | C | Val [V] | 3 | 279 |
| 1100 | rs373171169 | synonymous | A | Thr [T] | 3 | 271 |
| | | contig reference | G | Thr [T] | 3 | 271 |
| 1099 | rs147899611 | missense | T | Met [M] | 2 | 271 |
| | | contig reference | C | Thr [T] | 2 | 271 |
| 1059 | rs201671248 | synonymous | A | Arg [R] | 1 | 258 |
| | | contig reference | C | Arg [R] | 1 | 258 |
| 1054 | rs376228389 | missense | A | Glu [E] | 2 | 256 |
| | | contig reference | G | Gly [G] | 2 | 256 |
| 1001 | rs376292728 | synonymous | A | Thr [T] | 3 | 238 |
| | | contig reference | G | Thr [T] | 3 | 238 |
| 984 | rs141795046 | missense | A | Thr [T] | 1 | 233 |
| | | contig reference | G | Ala [A] | 1 | 233 |
| 983 | rs145552668 | synonymous | T | Ser [S] | 3 | 232 |
| | | contig reference | C | Ser [S] | 3 | 232 |

TABLE 2-continued

| | | | | | | |
|---|---|---|---|---|---|---|
| 953-954 | rs34000389 | frame shift | G | Gly [G] | 3 | 223 |
| | | contig reference | — | Ala [A] | 3 | 223 |
| 951 | rs147707423 | missense | G | Ala [A] | 1 | 222 |
| | | contig reference | A | Thr [T] | 1 | 222 |
| 932 | rs201983335 | synonymous | A | Pro [P] | 3 | 215 |
| | | contig reference | G | Pro [P] | 3 | 215 |
| 911 | rs145686330 | synonymous | A | Pro [P] | 3 | 208 |
| | | synonymous | T | Pro [P] | 3 | 208 |
| | | contig reference | C | Pro [P] | 3 | 208 |
| 909 | rs113899618 | missense | T | Ser [S] | 1 | 208 |
| | | contig reference | C | Pro [P] | 1 | 208 |
| 895 | rs375674516 | missense | G | Gly [G] | 2 | 203 |
| | | contig reference | A | Glu [E] | 2 | 203 |
| 845 | rs368575800 | synonymous | A | Ile [I] | 3 | 186 |
| | | contig reference | C | Ile [I] | 3 | 186 |
| 837 | rs148818548 | missense | A | Arg [R] | 1 | 184 |
| | | contig reference | G | Gly [G] | 1 | 184 |
| 755 | rs372890425 | synonymous | T | Pro [P] | 3 | 156 |
| | | contig reference | C | Pro [P] | 3 | 156 |
| 749 | rs375582985 | synonymous | A | Ser [S] | 3 | 154 |
| | | contig reference | G | Ser [S] | 3 | 154 |
| 731 | rs137930330 | synonymous | A | Gln [Q] | 3 | 148 |
| | | contig reference | G | Gln [Q] | 3 | 148 |
| 701 | rs369145467 | synonymous | A | Pro [P] | 3 | 138 |
| | | contig reference | G | Pro [P] | 3 | 138 |
| 681 | rs373908933 | synonymous | T | Leu [L] | 1 | 132 |
| | | contig reference | C | Leu [L] | 1 | 132 |
| 434 | rs368427729 | synonymous | A | Gly [G] | 3 | 49 |
| | | contig reference | G | Gly [G] | 3 | 49 |
| 402 | rs144204026 | missense | A | Arg [R] | 1 | 39 |
| | | contig reference | G | Gly [G] | 1 | 39 |

Determination of the Presence of a SMAD7 Polymorphic Variant in a Subject

The presence of a SMAD7 polymorphic variant can be accomplished using any method known in the art. In general, presence is detected in a sample taken from the patient. Identification of the presence of a SMAD7 polymorphism in a patient can be accomplished using standard techniques, including hybridization-based techniques, sequencing techniques, and array-based techniques.

The determination of the presence of a SMAD7 polymorphic variant can be detected in any biological sample and can be any specimen obtained from a patient or test subject that contains a nucleic acid (e.g., genomic DNA or RNA) that encodes SMAD7. Exemplary samples include a tissue biopsy, cell, bodily fluid (e.g., blood, serum, plasma, semen, urine, saliva, amniotic fluid, or cerebrospinal fluid).

Once obtained, the presence of a SMAD7 polymorphic variant can be detected using any appropriate method. In some embodiments, a hybridization approach is used. Hybridization approaches include dynamic allele-specific hybridization (Howell et al., Nat. Biotechnol. 17:87, 1999). This approach relies on differential melting temperatures between the sequence containing the polymorphism as compared to the sequence without the polymorphism. Briefly, a DNA region of interest is amplified by PCR using a biotinylated primer. The resulting PCR product is attached to a streptavidin support and is hybridized to an allele-specific probe in the presence of a DNA duplex-binding fluorescent molecule. The duplex is heated, and the temperature at which the duplex denatures is determined based on loss of fluorescence. The denaturation temperature is determinative of the presence or absence of the polymorphism.

Other approaches for detecting SNPs include the use of molecular beacons, as described in Mhlanga et al., Methods 25:463, 2001. This approach involves the use of single-stranded probe containing a stem-loop structure. The loop portion of the structure contains a sequence capable of hybridizing to the genomic DNA in question when the sequence matches exactly, and the ends of the stem contain, respectively, a fluorophore and a quencher. When the beacon binds to its target sequence, the fluorophore and quencher are separated, thus allowing fluorescence, which indicates the presence of the SNP.

Another hybridization approach for identifying the presence of SNPs is the use of nucleic acid arrays designed for this purpose. For example, the Genome-Wide Human SNP Array 6.0 (Affymetrix, Part #901182) can be used to detect the presence of certain SNPs in samples taken from a patient.

Still other approaches for identification of SNP include sequence approaches. As high throughput genomic screening (e.g., so-called "next-generation" sequencing) becomes technologically feasible, such approaches can also be used to identify the presence of SNPs within a patient. These approaches include single-molecule real time sequencing (Pacific Biosciences), ion semiconductor (Ion Torrent Sequencing; Life Technologies), pyrosequencing (454 Life Sciences), sequencing by synthesis (Illumina Inc.), and sequencing by ligation (SOLiD Sequencing; Applied Biosystems).

Patient Populations

The antisense oligonucleotide can be administered to any patient for which a decrease in SMAD7 activity is desirable. Because SMAD7 is known to be associated with inflammation in inflammatory bowel disorders such as ulcerative colitis and Crohn's disease, it can be beneficial to reduce SMAD7 activity in such patients.

The compositions and methods of the invention can be used to treat patients that are steroid-resistant, patients that are steroid-dependent, or patients that are resistant to another anti-SMAD7 therapy (e.g., resistant to treatment with an oligonucleotide that has a nucleotide mismatch relative to at least one of the corresponding nucleotides present in a patient's genome).

In particular embodiments, the patient is a subject identified as having altered levels of a biomarker that is associated with IBD or with inflammation. For example, the patient may have elevated levels of interleukin-8 (IL-8), tumor necrosis factor-α (TNF-α), or C-reactive protein (CRP) relative to a normal control or a normal control value.

In particular embodiments, a patient is selected if the patient shows some likelihood of responsiveness to anti-SMAD7 therapy. Likelihood of responsiveness to anti-SMAD7 therapy is premised in part on determining levels of CRP, TNFα, and/or IL8 in a patient with IBD, for example, preexisting levels of CRP, TNFα, and/or IL8 (i.e., levels of CRP, TNFα, and/or IL8 in a patient prior to administration of an initial dose of a SMAD7 antisense oligonucleotide) or levels of CRP, TNFα, and/or IL8 determined after an initial dose or one or more subsequent doses of SMAD7 antisense oligonucleotide. For instance, in some embodiments of the invention, a patient will be selected for treatment or further treatment with a SMAD7 antisense oligonucleotide after detecting or analyzing absolute or relative CRP, TNFα, and/or IL8 levels or changes in CRP, TNFα, and/or IL8 levels. Levels of CRP, TNFα, and/or IL8 in a patient with IBD may be compared to a normal level of CRP, TNFα, and/or IL8, for example, normal levels of CRP, TNFα, and/or IL8 as defined by median CRP, TNFα, and/or IL8 levels in a matched control group or absolute levels of CRP, TNFα, and/or IL8. In certain embodiments, a patient is selected for treatment with anti-SMAD-7 therapy if the CRP level in the blood is greater than 3.0 mg/ml, greater than 3.5 mg/ml, or greater than 4.0 mg/ml In some embodiments, a patient will be selected for treatment or further treatment with a SMAD7 antisense oligonucleotide if the levels of CRP, TNFα, and/or IL8 in the patient are more than 10%, 20%, 30%, 40%, 50%, 60%, 70%, 80%, 90%, or 100% elevated relative to the average, median or mean levels of CRP, TNFα, and/or IL8 in a matched control group.

In some embodiments, a patient will be selected for treatment or further treatment with a SMAD7 antisense oligonucleotide if the level of CRP, TNFα, and/or IL8 in the patient are more than 2-fold, more than 3-fold, more than 4-fold, more than 5-fold, more than 6-fold, more than 7-fold, more than 8-fold, more than 9-fold or more than 10-fold elevated relative to the average, median or mean levels of CRP, TNFα, and/or IL8 in a matched control group.

Typically CRP, TNFα, and/or IL8 levels will be measured in terms of a concentration, for instance, mass of CRP, TNFα, and/or IL8 protein, peptide, or RNA per volume of sample, for example, volume of blood or tissue. Thus, selection of patients for initial or continued treatment may be tied to CRP, TNFα, and/or IL8 levels in the patient, such that, for example, high initial levels of CRP, TNFα, and/or IL8 may indicate a potential for responsiveness to SMAD7 antisense oligonucleotide treatment. Furthermore, high levels of CRP, TNFα, and/or IL8 (i.e., above normal levels of IL8) may indicate a need for increased doses of SMAD7 antisense oligonucleotide, whereas normal or below normal levels of CRP, TNFα, and/or IL8 may indicate a need for decreased or unchanged doses of SMAD7 antisense oligonucleotide, especially following one or more doses. Alternatively, continued levels of above normal levels of CRP, TNFα, and/or IL8 after repeated doses may indicate that the patient is not responsive to treatment.

A control level of CRP, TNFα, and/or IL8 may be determined by determining the level of CRP, TNFα, and/or IL8 protein or mRNA transcript in a sample (e.g., a blood sample) obtained from the subject prior to treatment with an anti-SMAD7 therapy. The control level of CRP, TNFα, and/or IL8 may provide a baseline for monitoring a subject's response to treatment. A control sample may be obtained from the subject on the day the anti-SMAD7 therapy is first administered (e.g., Day 1 of a treatment regimen), for example, immediately after administration of at least one anti-SMAD7 therapy. In other embodiments, a control sample may be obtained from a subject one day prior to the start of an anti-SMAD7 therapy (e.g., Day 0 of a treatment regimen). Alternatively, a control sample may be obtained from a subject 2, 3, 4, 5, 6, 7, or more days prior to the start of an anti-SMAD7 therapy. For example, the increase or decrease in IL8 concentration may be measured prior to treatment (e.g., in a control sample), during treatment, and/or after treatment to monitor a subject's response to therapy, e.g., an anti-SMAD7 therapy.

In some embodiments, a control level may be established for a subject based on long-term monitoring of circulating CRP, TNFα, and/or IL8 concentration in the subject. In such instances, it is contemplated that a subject may undergo multiple rounds of treatment with an anti-SMAD7 therapy. The circulating CRP, TNFα, and/or IL8 concentration detected following multiple rounds of treatment may be compared to a prior control level of CRP, TNFα, and/or IL8 for the subject to determine whether the subject has responded to therapy and/or is likely to respond to further treatment with an anti-SMAD7 therapy. In other embodiments, a control or baseline level for a subject may be established based on an average measurement of a circulating CRP, TNFα, and/or IL8 concentration determined from multiple baseline samples obtained over time (e.g., obtained over the course of days, weeks, months, or years). Accordingly, any test or assay conducted as disclosed herein may be compared with a previous or established control level and it may not be necessary to obtain a new control sample from the subject for comparison, e.g., if the subject is receiving more than one round of treatment with an anti-SMAD7 therapy.

Normal levels of CRP, TNFα, and/or IL8 may be determined based on numerical reference values or with respect to levels of CRP, TNFα, and/or IL8 in a healthy control group.

In other embodiments of the invention, normal levels of CRP, TNFα, and/or IL8 are defined as median levels of CRP, TNFα, and/or IL8 in a healthy control group.

A healthy control group may be defined based on various criteria related to genetic background, habits, and physical attributes matched to the same set of criteria in the patient. For instance, in some embodiments, the healthy control group and the patient having IBD are matched with respect to age, gender, ethnic origin, smoking habits, dietary habits, body-mass index (BMI), recreational drug use, medical drug use, drug use related to IBD, and/or exercise habits. Other factors that can be matched between the patient and control group include, but are not limited to, clinical criteria (e.g., CDAI score, Mayo score, severity of IBD-related symptoms), metabolism, IBD patient's personal disease history, genetic factors, IBD patient's family disease history, exposure to environmental factors (e.g., pollutants, toxins, allergens), and life-style (e.g., urban, suburban, or rural place of work and/or domicile).

In some embodiments, the control group is the patient receiving a treatment with an SMAD7 antisense oligonucleotide prior to receiving an initial dose of the SMAD7 antisense oligonucleotide. In some embodiments, the patient is a treatment naive patient.

SMAD7 Antisense Oligonucleotides

The anti-SMAD7 antisense oligonucleotides used in the methods and compositions described herein are specifically targeted to the patient's specific SMAD7 sequence (e.g., containing one or more polymorphisms). The SMAD7 antisense oligonucleotide may incorporate a sequence that corresponds to the presence of any polymorphism in SMAD7, e.g., a polymorphism detected in a patient. The polymorphism may include any of those described in the SMAD7 transcript (see, e.g., Table 1) or in the SMAD7 coding region (see, e.g., Table 2).

In one example, the SMAD7 oligonucleotide sequence is that of Mongersen (SEQ ID NO:7). This sequence targets nucleic acids 108-128 of the SMAD7 coding sequence (SEQ ID NO:1, which corresponds to nucleotides 396-416 of the mRNA transcript of Accession number NM_005904.3). This region contains SNP rs144204026, which involves a G→A substitution. For patients having one or two copies of this polymorphism, an antisense oligonucleotide containing the corresponding polymorphism in its sequence can be used (e.g., SEQ ID NOS:10-13). Antisense oligonucleotides provided herein can increase efficacy in reducing SMAD7 expression relative to an oligonucleotide that lacks the exact corresponding sequence.

Where the patient is heterozygous for a polymorphism (i.e., has one copy of the SMAD7 gene that contains the polymorphism such as SNP rs144204026 and one copy of the SMAD7 containing the consensus sequence) within the antisense sequence, it can be desirable to administer a combination of antisense oligonucleotides, either as a mixture or in two separate compositions, one that corresponds to the consensus sequence (e.g., SEQ ID NO:1 and NM_005904.3) and one that corresponds to the sequence containing the polymorphism (e.g., SEQ ID NOS:9 and 10). The appropriate oligonucleotide or combination of oligonucleotides for any particular patient can be determined based on whether the patient in question is carrier of the polymorphism. Identification of the presence (or absence) of any polymorphism can be achieved, for example, using any of the methods described herein.

It will be recognized by a skilled artisan that some SMAD7 antisense oligonucleotides targeting a consensus sequence, e.g., the SMAD7 antisense oligonucleotide including the nucleotide sequence of SEQ ID NO:7, can be administered to a patient that is homozygous or heterozygous for a SMAD7 polymorphism lacking the exact corresponding target sequence of the antisense oligonucleotide, e.g., the SMAD7 antisense oligonucleotide including the nucleotide sequence of SEQ ID NO:7. Such SMAD7 antisense oligonucleotides, e.g., the SMAD7 antisense oligonucleotide including the nucleotide sequence of SEQ ID NO:7, can reduce the expression of SMAD7 polymorphic forms lacking the exact corresponding target sequence of the antisense oligonucleotide.

In certain embodiments, an anti-SMAD7 antisense oligonucleotide may target site 403, 233, 294, 295, 296, 298, 299, and/or 533 (i.e., nucleotides 403, 233, 294, 295, 296, 298, 299, and 533, respectively) of the human SMAD7 mRNA (e.g., NCBI Reference NM_005904.3). The rs144204026 polymorphism described above is at position 402 of the human SMAD7 sequence. Thus oligonucleotides targeting nucleotide 403 can be designed to incorporate the rs144204026 polymorphism. In other examples, oligonucleotides that target sites 294, 295, 296, 298, or 299 (e.g., 294, 295, or 296) may target the SMAD7 mRNA containing the rs374325868 polymorphism at position 277 of the transcript.

The antisense oligonucleotide targeting SMAD7 may comprise a mixed-backbone wherein the cytosine residues in a CpG pair are replaced by 5'-methylcytosine (abbreviated as Me-dC). Methylphosphonate linkages may also be placed at the 5' and/or 3' ends of an antisense oligonucleotide (abbreviated as MeP).

Exemplary antisense oligonucleotide therapies that target polymorphic forms of SMAD7 include, but are not limited to 5'-GTXYCCCCTTCTCTCXYCAGC-3' (SEQ ID NO:21), wherein X is a nucleotide comprising a nitrogenous base selected from the group consisting of cytosine and 5-methylcytosine or a 2'-O-methylcytosine nucleotide, and wherein Y is a nucleotide comprising a nitrogenous base selected from the group consisting of guanine and 5-methylguanine or a 2'-O-methylguanine nucleotide, optionally provided that at least one of the nucleotides X or Y comprises a methylated nitrogenous base;

5'-GTXGCCCCTTCTCTCXGCAG-3' (SEQ ID NO:12), wherein X is 5-methyl 2'-deoxycytidine and wherein all internucleotide linkages are phosphorothioate linkages;

5'-GTXGCCCCTTCTCTCXGCAGC-3' (SEQ ID NO:13), wherein X is 5-methyl 2'-deoxycytidine and wherein all internucleotide linkages are phosphorothioate linkages;

5'-ZTXGCCCCTTCTCTCXGCAZ-3' (SEQ ID NO:18), wherein X is 5-methyl 2'-deoxycytidine and Z is 2'-deoxyguanosine methylphosphonate;

5'-ZTXGCCCCTTCTCTCXGCAZC-3' (SEQ ID NO:19), wherein X is 5-methyl 2'-deoxycytidine and Z is 2'-deoxyguanosine methylphosphonate;

5'-GTXGCCCCTTCTCTCXGCAGC-3' (SEQ ID NO:20), wherein X is 5-methyl 2'-deoxycytidine.

Disclosed therapies may, when administered orally to a subject suffering from IBD, deliver an effective amount of an antisense oligonucleotide to the intestinal system of a patient, e.g., deliver an effective amount of an antisense oligonucleotide to the terminal ileum and/or right colon of a patient.

Contemplated antisense oligonucleotides include those comprising SEQ ID NO:5 or SEQ ID NO:11: 5'-GTC*GCC CCT TCT C(C/T)C C*GC AGC-3', where C* represents 5-methyl-2'-deoxycytidine. In some embodiments, at least one of the internucleotide linkages of a contemplated antisense oligonucleotide is an O,O-linked phosphorothioate, for example, each of the 20 internucleotide linkages of SEQ ID NO:5 may be an O,O-linked phosphorothioate. In some embodiments, the contemplated antisense oligonucleotide is an antisense oligonucleotide comprising SEQ ID NO:7 or 13, wherein each of the 20 internucleotide linkages is an O,O-linked phosphorothioate linkage. In a particular embodiment, the contemplated antisense oligonucleotide is an antisense oligonucleotide comprising SEQ ID NO:7, wherein each of the 20 internucleotide linkages is an O,O-linked phosphorothioate linkage, referred to herein as "Mongersen." In some embodiments, contemplated compositions disclosed herein may include a pharmaceutically acceptable salt, e.g., a sodium salt of the antisense oligonucleotide of SEQ ID NOs:5, 7, 11 or 13, that optionally may include 1 to 20 O,O-linked phosphorothioate internucleotide linkages. Contemplated salts of oligonucleotides include those that are fully neutralized, e.g., each phosphorothioate linkage is associated with an ion such as $Na^+$. Oligonucleotides may include naturally occurring nucleobases, sugars, and covalent internucleotide (backbone) linkages as well as non-naturally occurring portions.

Table 3 lists the target sequences of exemplary SMAD7 antisense oligonucleotides and the regions in the SMAD7 coding sequence of SEQ ID NO: 1 that are targeted by the SMAD7 antisense oligonucleotides. Target sequences are shown as DNA target sequences. However, the corresponding RNA target sequences can also be targeted by the listed SMAD7 antisense oligonucleotides of Table 3.

prepared by methods well known in the pharmaceutical art. For example, see *Remington's Pharmaceutical Sciences*, $22^{nd}$ ed. (Pharmaceutical Press and Philadelphia College of Pharmacy at University of the Sciences, 2012).

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

Oral Administration

In some embodiments of the invention, the anti-SMAD7 therapy may be suitable for oral delivery, e.g., tablets, that include an enteric coating, e.g., a gastro-resistant coating, such that the compositions may deliver the antisense compound to, e.g., the terminal ileum and right colon of a patient. For example, such administration may result in a topical effect, substantially topically applying the antisense compound directly to an affected portion of the intestine of a subject. Such administration, may, in some embodiments, substantially avoid unwanted systemic absorption of the antisense compound.

For example, a tablet for oral administration may comprise granules (e.g., is at least partially formed from granules) that include a disclosed antisense compound, e.g., the SMAD7 antisense oligonucleotides provided herein, and pharmaceutically acceptable excipients. Such a tablet may

TABLE 3

| SMAD7 Antisense Oligonucleotide (SEQ ID NO) | SMAD7 Antisense Oligonucleotide Target Sequence* | Position in SEQ ID NO: 1 Or Polymorphic Forms of SEQ ID NO: 1 |
|---|---|---|
| SEQ ID NO: 4 | 5'-CTGCGGGGAGAAGGGGCGAC-3' | Positions 109-128 |
| SEQ ID NO: 5 | 5'-GCTGCGGGGAGAAGGGGCGAC-3' | Positions 108-128 |
| SEQ ID NO: 6 | 5'-CTGCGGGGAGAAGGGGCGAC-3' | Positions 109-128 |
| SEQ ID NO: 7 | 5'-GCTGCGGGGAGAAGGGGCGAC-3' | Positions 108-128 |
| SEQ ID NO: 10 | 5'-CTGCGGAGAGAAGGGGCGAC-3' | Positions 109-128 |
| SEQ ID NO: 11 | 5'-GTGCGGAGAGAAGGGGCGAC-3' | Positions 108-128 |
| SEQ ID NO: 12 | 5'-CTGCGGAGAGAAGGGGCGAC-3' | Positions 109-128 |
| SEQ ID NO: 13 | 5'-GCTGCGGAGAGAAGGGGCGAC-3' | Positions 108-128 |
| SEQ ID NO: 14 | 5'-GCTGCGGGGAGAAGGGGCGAC-3' | Positions 108-128 |
| SEQ ID NO: 15 | 5'-GCTGCGGGGAGAAGGGGCGAC-3' | Positions 108-128 |
| SEQ ID NO: 16 | 5'-GCTGCGGGGAGAAGGGGCGAC-3' | Positions 108-128 |
| SEQ ID NO: 17 | 5'-GCTGCGGGGAGAAGGGGCGAC-3' | Positions 108-128 |
| SEQ ID NO: 18 | 5'-CTGCGGAGAGAAGGGGCGAC-3' | Positions 109-128 |
| SEQ ID NO: 19 | 5'-GCTGCGGAGAGAAGGGGCGAC-3' | Positions 108-128 |
| SEQ ID NO: 20 | 5'-GCTGCGGAGAGAAGGGGCGAC-3' | Positions 108-128 |
| SEQ ID NO: 21 | 5'-GCTGCGGAGAGAAGGGGCGAC-3' | Positions 108-128 |

*Target sequences are shown as DNA sequences and can alternatively be RNA sequences, with Ts replaced by Us.

Pharmaceutical Compositions

Pharmaceutical compositions containing an antisense oligonucleotide against SMAD7, such as those disclosed herein, can be presented in a dosage unit form and can be prepared by any suitable method. A pharmaceutical composition should be formulated to be compatible with its intended route of administration. Useful formulations can be be coated with an enteric coating. Contemplated tablets may include pharmaceutically acceptable excipients such as fillers, binders, disintegrants, and/or lubricants, as well as coloring agents, release agents, coating agents, sweetening, flavoring such as wintergreen, orange, xylitol, sorbitol, fructose, and maltodextrin, and perfuming agents, preservatives and/or antioxidants.

In some embodiments, contemplated pharmaceutical formulations include an intra-granular phase that includes a contemplated antisense compound or a pharmaceutically acceptable salt, e.g., the SMAD7 antisense oligonucleotides provided herein, and a pharmaceutically acceptable filler. For example, a SMAD7 antisense oligonucleotide provided herein and a filler may be blended together, with optionally other excipients, and formed into granules. In some embodiments, the intragranular phase may be formed using wet granulation, e.g., a liquid (e.g., water) is added to the blended antisense compound and filler, and then combination is dried, milled and/or sieved to produce granules. One of skill in the art would understand that other processes may be used to achieve an intragranular phase.

In some embodiments, contemplated formulations include an extra-granular phase, which may include one or more pharmaceutically acceptable excipients, and which may be blended with the intragranular phase to form a disclosed formulation.

An anti-SMAD7 therapy formulation may include an intragranular phase that includes a filler. Exemplary fillers include, but are not limited to, cellulose, gelatin, calcium phosphate, lactose, sucrose, glucose, mannitol, sorbitol, microcrystalline cellulose, pectin, polyacrylates, dextrose, cellulose acetate, hydroxypropylmethyl cellulose, partially pregelatinized starch, calcium carbonate, and others including combinations thereof.

In some embodiments, an anti-SMAD7 therapy formulation may include an intragranular phase and/or an extra-granular phase that includes a binder, which may generally function to hold the ingredients of the pharmaceutical formulation together. Exemplary binders include invention may be, but are not limited to, the following: starches, sugars, cellulose or modified cellulose such as hydroxypropyl cellulose, lactose, pregelatinized maize starch, polyvinyl pyrrolidone, hydroxypropyl cellulose, hydroxypropylmethyl cellulose, low substituted hydroxypropyl cellulose, sodium carboxymethyl cellulose, methyl cellulose, ethyl cellulose, sugar alcohols and others including combinations thereof.

Contemplated anti-SMAD7 therapy formulations, e.g., that include an intragranular phase and/or an extragranular phase, may include a disintegrant such as but are not limited to, starch, cellulose, crosslinked polyvinyl pyrrolidone, sodium starch glycolate, sodium carboxymethyl cellulose, alginates, corn starch, crosmellose sodium, crosslinked carboxymethyl cellulose, low substituted hydroxypropyl cellulose, acacia, and others including combinations thereof. For example, an intragranular phase and/or an extragranular phase may include a disintegrant.

In some embodiments, a contemplated anti-SMAD7 therapy formulation includes an intra-granular phase comprising a disclosed antisense compound and excipients chosen from mannitol, microcrystalline cellulose, hydroxypropylmethyl cellulose, and sodium starch glycolate or combinations thereof, and an extra-granular phase comprising one or more of microcrystalline cellulose, sodium starch glyco late, and magnesium stearate or mixtures thereof.

In some embodiments, a contemplated anti-SMAD7 therapy formulation may include a lubricant, e.g., an extragranular phase may contain a lubricant. Lubricants include but are not limited to talc, silica, fats, stearin, magnesium stearate, calcium phosphate, silicone dioxide, calcium silicate, calcium phosphate, colloidal silicon dioxide, metallic stearates, hydrogenated vegetable oil, corn starch, sodium benzoate, polyethylene glycols, sodium acetate, calcium stearate, sodium lauryl sulfate, sodium chloride, magnesium lauryl sulfate, talc, and stearic acid.

In some embodiments, the pharmaceutical formulation comprises an enteric coating. Generally, enteric coatings create a barrier for the oral medication that controls the location at which the drug is absorbed along the digestive track. Enteric coatings may include a polymer that disintegrates a different rates according to pH. Enteric coatings may include, for example, cellulose acetate phthalate, methyl acrylate-methacrylic acid copolymers, cellulose acetate succinate, hydroxylpropylmethyl cellulose phthalate, methyl methacrylate-methacrylic acid copolymers, ethylacrylate-methacrylic acid copolymers, methacrylic acid copolymer type C, polyvinyl acetate-phthalate, and cellulose acetate phthalate.

Exemplary enteric coatings include Opadry® AMB, Acryl-EZE®, Eudragit® grades. In some embodiments, an enteric coating may comprise about 5% to about 10%, about 5% to about 20%, 8 to about 15%, about 8% to about 18%, about 10% to about 12%, or about 12 to about 16%, of a contemplated tablet by weight. For example, enteric coatings may include an ethylacrylate-methacrylic acid copolymer.

In one embodiment, the anti-SMAD7 therapy may be a tablet for oral use comprising: about 0.5% to about 10% by weight of an antisense oligonucleotide described herein or a pharmaceutically acceptable salt thereof; about 30% to about 50% by weight mannitol; and about 10% to about 30% by weight microcrystalline cellulose.

For example, an anti-SMAD7 therapy in the form of a tablet is provided that comprises or consists essentially of about 0.5% to about 70%, e.g., about 0.5% to about 10%, or about 1% to about 20%, by weight of an antisense oligonucleotide or a pharmaceutically acceptable salt thereof (e.g., a SMAD7 antisense oligonucleotide provided herein). Such a tablet may include for example, about 0.5% to about 60% by weight of mannitol, e.g., about 30% to about 50% by weight mannitol, e.g., about 40% by weight mannitol; and/or about 20% to about 40% by weight of microcrystalline cellulose, or about 10% to about 30% by weight of microcrystalline cellulose. For example, a contemplated tablet may comprise an intragranular phase that includes about 30% to about 60%, e.g., about 45% to about 65% by weight, or alternatively, about 5% to about 10% by weight of a SMAD7 antisense oligonucleotide provided herein, about 30% to about 50%, or alternatively, about 5% to about 15% by weight mannitol, about 5% to about 15% microcrystalline cellulose, about 0% to about 4%, or about 1% to about 7% hydroxypropylmethylcellulose, and about 0% to about 4%, e.g., about 2% to about 4% sodium starch glycolate by weight.

In an exemplary embodiment of the invention, a pharmaceutically acceptable tablet for oral administration is provided that includes an intra-granular phase that may comprise about 50% by weight of a SMAD7 antisense oligonucleotide provided herein (or salt thereof), about 11.5% by weight mannitol, about 10% by weight microcrystalline cellulose, about 3% by weight hydroxypropylmethylcellulose, and about 2.5% by weight sodium starch glycolate; and an extra-granular phase that may comprise about 20% by weight microcrystalline cellulose, about 2.5% by weight sodium starch glycolate, and about 0.5% by weight magnesium stearate. The tablet may also include an enteric coating.

In another exemplary embodiment, a pharmaceutically acceptable tablet for oral administration is provided that includes or consists essentially of: an intra-granular phase that may comprise or consist essentially of about 5% to about 10%, e.g., about 8% by weight of a SMAD7 antisense oligonucleotide provided herein (e.g., wherein the internucleotide linkages are each O,O-linked phophorothioates, and/or salt thereof, e.g., a sodium salt), about 40% by weight mannitol, about 8% by weight microcrystalline cellulose, about 5% by weight hydroxypropylmethylcellulose, and about 2% by weight sodium starch glycolate; and an extragranular phase that may comprise about 17% by weight microcrystalline cellulose, about 2% by weight sodium starch glycolate, and about 0.4% by weight magnesium stearate.

Parenteral Administration

The pharmaceutical compositions of the invention can be formulated for parenteral administration, e.g., formulated for injection via the intravenous, intramuscular, subcutaneous, intralesional, or intraperitoneal routes. The preparation of an aqueous composition, such as an aqueous pharmaceutical composition containing a SMAD7 inhibitor, will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. In addition, sterile, fixed oils may be employed as a solvent or suspending medium. For this purpose any bland fixed oil can be employed including synthetic mono- or diglycerides. In addition, fatty acids such as oleic acid can be used in the preparation of injectables. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In one embodiment, the SMAD7 inhibitor may be suspended in a carrier fluid comprising 1% (w/v) sodium carboxymethylcellulose and 0.1% (v/v) TWEEN™ 80. Under ordinary conditions of storage and use, these preparations contain a preservative to prevent the growth of microorganisms.

Injectable preparations, for example, sterile injectable aqueous or oleaginous suspensions may be formulated according to the known art using suitable dispersing or wetting agents and suspending agents. Generally, dispersions are prepared by incorporating the various sterilized active ingredients into a sterile vehicle which contains the basic dispersion medium and the required other ingredients from those enumerated above. Sterile injectable solutions of the invention may be prepared by incorporating a SMAD7 inhibitor in the required amount of the appropriate solvent with various of the other ingredients enumerated above, as required, followed by filtered sterilization. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The injectable formulations can be sterilized, for example, by filtration through a bacteria-retaining filter.

The preparation of more, or highly, concentrated solutions for intramuscular injection is also contemplated. In this regard, the use of DMSO as solvent is preferred as this will result in extremely rapid penetration, delivering high concentrations of the SMAD7 inhibitor to a small area.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium 10 carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose and the like.

In an exemplary embodiment, a pharmaceutical composition for subcutaneous administration of an antisense oligonucleotide against SMAD7 comprises an antisense oligonucleotide such as that represented by SEQ ID NO: 7, or a pharmaceutically acceptable salt thereof (such as a sodium salt), and a pharmaceutically acceptable carrier.

Contemplated tablets may also include an enteric coating, e.g., a disclosed tablet may include about 13%, about 14%, about 15%, about 16%, about 17% by weight of an enteric coating, e.g., ethylacrylate-methacrylic acid copolymers (e.g., AcrylEZE®).

For example, the anti-SMAD7 therapy may be in the form of a pharmaceutically acceptable tablet for oral use comprising an intra-granular phase and extra-granular phase, wherein for example, the intra-granular phase comprises about 5% to about 10%, by weight (for example about 8% by weight) of an antisense oligonucleotide represented by SEQ ID NO:7 or a pharmaceutically acceptable salt thereof, about 40% by weight mannitol, about 8% by weight microcrystalline cellulose, about 5% by weight hydroxypropylmethyl cellulose, and about 2% by weight sodium starch glycolate, and for example, the extra-granular phase comprises about 17% by weight microcrystalline cellulose, about 2% by weight sodium starch glycolate, and about 0.4% by weight magnesium stearate, where the tablet may further comprise an enteric coating.

Contemplated formulations, e.g., tablets, in some embodiments, when orally administered to the patient may result in minimal plasma concentration of the oligonucleotide in the patient. In another embodiment, contemplated formulations, when orally administered to a patient, topically deliver to the terminal ileum and/or right colon of a patient, e.g., to an affected or diseased intestinal site of a patient.

Administration and Dosing

Exemplary formulations include dosage forms that include or consist essentially of about 10 mg to about 500 mg of an antisense oligonucleotide against SMAD7. For example, formulations that include about 10 mg, about 15 mg, about 20 mg, about 25 mg, about 30 mg, about 35 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 200 mg, or about 250 mg of an antisense oligonucleotide against SMAD7 are contemplated herein. In one embodiment, a formulation may include about 40 mg, 80 mg, or 160 mg of an antisense oligonucleotide against SMAD7. In some embodiments, a formulation may include at least 100 µg of an antisense oligonucleotide against SMAD7. For example, formulations may include about 0.1 mg, 0.2 mg, 0.3 mg, 0.4 mg, 0.5 mg, 1 mg, 5 mg, 10 mg, 15 mg, 20 mg, or 25 mg of an antisense oligonucleotide against SMAD7. The amount administered will depend on variables such as the type and extent of disease or indication to be treated, the overall health and size of the patient, the in vivo potency of the antisense oligonucleotide, the pharmaceutical formulation, and the route of administration. The initial dosage can be increased beyond the upper level in order to rapidly achieve the desired blood-level or tissue level. Alternatively, the initial dosage can be smaller than the optimum, and the dosage may be progressively increased during the course of treatment. Human dosage can be optimized, e.g., in a conventional Phase I dose escalation study designed to run from 40 mg to 160 mg. Dosing frequency can vary, depending on factors such as route of administration, dosage amount and the disease being treated. Exemplary dosing frequencies are once per day, once per week and once every two weeks. In some embodiments, dosing is once per day for 7 days.

Concomitant Treatments

In some embodiments of the invention, the anti-SMAD7 therapy may be administered following or concurrently with other treatments, for instance, but not limited to, a steroid or steroids, an immunomodulator or immunomodulators, and/or mesalamine. The anti-SMAD7 therapy may be administered following or concurrently with any combination of these treatments. For instance, in some embodiments, the anti-SMAD7 therapy may be administered with only a steroid or steroids, only an immunomodulator or immunomodulators, only mesalamine, a steroid or steroids and an immunomodulator or immunomodulators, a steroid or steroids and mesalamine, or an immunomodulator or immunomodulators and mesalamine.

Examples of immunomodulators include azathioprine, mercaptopurine, methotrexate, cyclosporine A, and tacrolimus. Examples of steroids include corticosteroids, for example, prednisone, dexamethasone, hydrocortisone, methylprednisolone, prednisone, and budesonide. In some embodiments, a different salicylate, for example, sulfasalazine, may be administered in place of mesalamine. In some embodiments of the invention, the steroid(s), immunomodulator(s), or mesalamine may be administered by the same route as the anti-SMAD7 therapy (i.e., orally). In some embodiments of the invention the steroid(s), immunomodulator(s), or mesalamine may be administered by a different route than the anti-SMAD7 therapy. For instance, the steroid(s), immunomodulator(s), or mesalamine may be administered parenterally, rectally, intravenously, topically, or by inhalation spray.

Monitoring Therapy

The effectiveness of the antisense therapy in treating inflammatory bowel disease can be monitored using any appropriate approach. For example, any of the biomarkers known to be associated with inflammatory bowel disease or excess SMAD7 activity can be used to monitor the effectiveness of therapy in a patient as can any subjective or objective clinical scale. Monitoring treatment may be useful in terms of assessing treatment efficacy and safety, as well as evaluating the need to modulate treatment. Monitoring treatment may also be useful for evaluating whether the amount of SMAD7 antisense oligonucleotide being administered to a patient or which will be administered to a patient should be increased or decreased or whether the antisense is effective. Furthermore, monitoring treatment may be useful in terms of determining the amount or relative amount by which a dose of SMAD7 antisense oligonucleotide should be modulated, i.e., increased or decreased.

Monitoring, for example, the level of a biomarker or a combination of biomarkers (e.g., CRP, TNFα, and IL8) in a patient having IBD, may commence prior to, during, or after an initial dose of a SMAD7 antisense oligonucleotide. Furthermore, monitoring may continue after an initial dose. For example monitoring may be performed after administration of an initial dose. Monitoring may also be performed before, during, or after a subsequent dose of SMAD7 antisense oligonucleotide. Monitoring may be continuous or discontinuous such that monitoring may be performed at regular intervals, for example, after each dose of a SMAD7 antisense oligonucleotide is administered to a patient, before each dose of a SMAD7 antisense oligonucleotide is administered to a patient, or before and after each dose of a SMAD7 antisense oligonucleotide is administered to a patient. Monitoring may be performed multiple times in a single day (for instance, 2 times, 3 times, 4 times, about five times, or about 10 times in a single day), once a day, multiple times in a single week (for instance, 2 times, 3 times, 4 times, about five times, or about 10 times in a single week), once a week, multiple times in a single month (for instance, 2 times, 3 times, 4 times, about five times, or about 10 times in a single month), or once a month. In methods of the invention, monitoring may be performed at various times relative to an administering step. For instance, in some embodiments, monitoring may be performed immediately after, or at least 1 day, at least 3 days, at least 5 days, at least 1 week, at least 2 weeks, at least 3 weeks, at least 1 month, at least 2 months, at least 4 months, or at least 6 months after an administration step. In some embodiments, monitoring is performed about 15 days or about 28 days after an administration step.

In some instances it will be useful to know a threshold value for normal or abnormal levels of the biomarker in order to determine whether levels of the SMAD7 antisense oligonucleotide should be increased, decreased, or left untouched. A normal level of CRP can be tied to a specific value, for instance, a value of about 0.01 mg/L, about 0.05 mg/L, about 0.1 mg/L, about 0.2 mg/L, about 0.3 mg/L, about 0.4 mg/L, about 0.5 mg/L, about 0.6 mg/L, about 0.7 mg/L, about 0.8 mg/L, about 0.9 mg/L, about 1.0 mg/L, about 1.5 mg/L, about 2.0 mg/L, about 2.5 mg/L, or about 3.0 mg/L. A normal level of TNFα may be about 11 µg/L (e.g., 11.2 µg/L), or may be another value (e.g., 5, 6, 7, 8, 9, 10, 12, 13, 14, or 15 µg/L), depending on the control subject. A normal level of IL8 in serum may be about 13 µg/L (e.g., 12.9 µg/L), or may be another value (e.g., 6, 7, 8, 9, 10, 11, 12, 14, 15, 16, or 17 µg/L), depending on the control subject. See, e.g., Arican et al., Mediators Inflamm. 2005:273, 2005. In some embodiments, a normal level of the biomarker may be determined by comparison to median levels of the biomarker in a healthy control group that is matched to the patient with respect to various factors, for example, age, gender, ethnic origin, smoking habits, dietary habits, body-mass index (BMI), and/or exercise habits.

Levels of a biomarker or combination of biomarkers (e.g., CRP, TNFα, and IL8) may be determined by obtaining a sample from the patient. According to the methods described herein, a sample may be a tissue sample (e.g., a gastrointestinal tissue sample) or a bodily fluid sample (e.g., a saliva sample, a stool, a urine sample, or any liquid biopsy). Samples may include solid tissue biopsies that contain biomarker-expressing cells, for example, epithelial colon tissue cells. A sample can be a sample obtained from a patient tissue biopsy, for example, a mucosal tissue biopsy, for example, an intestinal mucosal tissue biopsy. Furthermore, the sample may be a blood, serum, or plasma sample. A blood sample from a subject may be obtained using techniques well-known in the art. Blood samples may include peripheral blood mononuclear cells (PMBCs), RBC-depleted whole blood, or blood serum. PBMCs can be separated from whole blood samples using different density gradient (e.g., Ficoll density gradient) centrifugation procedures. For example, whole blood (e.g., anticoagulated whole blood) is layered over the separating medium and centrifuged. At the end of the centrifugation step, the following layers are visually observed from top to bottom: plasma/platelets, PBMC, separating medium and erythrocytes/granulocytes.

Samples may also be obtained or extracted from the patient based on temporal parameters. For instance, samples may be taken from the same patient at different time points, for example, about every 30 minutes, about every hour, about every three hours, about every 6 hours, or about every 12 hours, throughout a given time period, for example, about 1 hour, about 6 hours, about 12 hours, about 1 day, about 3 days, about 1 week, or about 1 month. Samples may also be taken after individual meals, for example, immediately after, about 30 minutes after, about 1 hour after, about 2 hours after, about 3 hours after, about 4 hours after, about 5 hours after, or about 6 hours after a meal.

Methods of monitoring treatment may also include methods of monitoring other factors, including, but not limited to levels of biomarkers (e.g., CRP, TNFα, and IL8), CDAI score, clinical remission, and presence or severity of IBD symptoms.

In embodiments of the invention where levels of a biomarker or a combination of biomarkers (e.g., CRP, TNFα, and IL8) are measured, various methods may be used to measure the biomarker. For example, the level of a biomarker, for example, IL8, TNFα, or CRP, may be determined by immunochemistry and/or by nucleotide analysis. For example, the amount of a biomarker in a blood or tissue sample, or a fraction of a blood or tissue sample of a known volume may be determined by immunochemistry. Methods of determining biomarker concentration by immunochemistry include, but are not limited to, Western blotting, ELISA, and immunostaining methods. In some embodiments, a method of determining biomarker concentration by immunochemistry is performed using an antibody that can bind to the biomarker of interest, for instance, an antibody directed against the biomarker. Assaying biomarker concentration by immunochemistry requires, for example, at least one antibody against the biomarker. A primary antibody may be tagged with a detectable label, e.g., a fluorescent marker. Alternatively, a secondary antibody tagged with a detectable label, e.g., a fluorescent marker, that binds specifically to the species isotype of the primary antibody may be used to perform immunochemistry. Methods of determining biomarker concentration by immunochemistry may also involve the use of buffers, blocking reagents, unconjugated primary antibodies, and primary and/or secondary antibodies conjugated to tags that allow for antibody detection, such as fluorescent probes or substrate-specific enzymes.

Methods of determining biomarker concentration by nucleotide analysis include, but are not limited to, methods of analyzing biomarker mRNA transcript levels such as Northern blotting and polymerase chain reaction methods, for example, quantitative polymerase chain reaction methods. Nucleotide analysis may be performed using an oligonucleotide probe that binds an biomarker nucleotide sequence (e.g., an CRP nucleotide sequence) or a pair of oligonucleotide primers capable of amplifying an biomarker nucleotide sequence via a polymerase chain reaction, for example, by a quantitative polymerase chain reaction. Oligonucleotide probes and oligonucleotide primers may be linked to a detectable tag, such as, for example, a fluorescent tag. In determining biomarker concentration by nucleotide analysis, the practitioner may evaluate a particular biomarker's mRNA transcript concentration in a sample. Alternatively, in determining biomarker concentration by nucleotide analysis, the practitioner may establish a correlation between a particular biomarker's mRNA transcript abundance and the particular biomarker's protein abundance in order to extrapolate biomarker protein concentration based on a measure of biomarker mRNA transcript abundance.

Methods of the claimed invention include steps that may be carried out in vitro. For instance, it is contemplated that the steps of measuring biomarker levels in the subject, determining the levels of the biomarker in a sample, and/or determining CDAI score or taking measurements necessary to determine CDAI score may be carried out in vitro. For example, the level of a biomarker in a sample may be determined by performing immunochemistry or nucleotide analysis on the sample in vitro. Alternatively, in some embodiments of the invention, the steps of determining and analyzing the biomarker level in a patient having IBD, determining and analyzing the biomarker level in a sample, and/or determining CDAI score or taking measurements necessary to determine CDAI score may be carried out in vivo.

Anti-IL8 antibodies suitable for immunochemistry are commercially available, including, but not limited to, goat anti-human IL8 from Abcam (Cat. No. ab10769), mouse anti-human IL8 from Santa Cruz (Cat. Nos. sc-73321, sc-52870, and sc-7302), mouse anti-human IL8 (3IL8-H10) from Pierce (Cat. No. M801), and a mouse anti-human IL8 from Sigma-Aldrich (Cat. No. WH0003576M5) antibody.

Anti-TNFα antibodies suitable for immunochemistry are commercially available, including, but not limited to, rabbit anti-human TNFα from Abcam (Cat. No. ab9635), rabbit anti-human TNFα from Cell Signaling Technology (Cat. No. 3707), mouse anti-human TNFα from affymetrix eBioscience (Cat. No. 14-7348-81), and rabbit anti-human TNFα from Rockland Antibodies & Assays (Cat. No. 209-401-306S) antibody.

Anti-CRP antibodies suitable for immunochemistry are commercially available, such as, for example, goat anti-human CRP polyclonal antibodies from Santa Cruz Biotechnology (Catalog Numbers sc-18304 and sc-18306), a rabbit anti-human CRP polyclonal antibody from from Santa Cruz Biotechnology (Catalog Number sc-30047), a mouse anti-human CRP monoclonal antibody from Santa Cruz Biotechnology (Catalog Number sc-70883), a mouse anti-human CRP monoclonal antibody from Sigma-Aldrich (Catalog Number C1688-2ML), a rabbit anti-human monoclonal antibody from abcam (Catalog Number ab32412), a mouse anti-human CRP monoclonal antibody from abcam (Catalog Number ab13426), and a goat anti-human CRP polyclonal antibody from Thermo Scientific (Catalog Number G0301-1B).

The invention now being generally described, it will be more readily understood by reference to the following examples which are included merely for purposes of illustration of certain aspects and embodiments of the present invention, and are not intended to limit the invention in any way.

EXAMPLES

Example 1—a Patient Heterozygous for the rs144204026 SNP

A patient is diagnosed with Crohn's disease. Prior to beginning therapy, the patient's SMAD7 gene sequence is analyzed in the patient using standard sequencing techniques to determine the presence or absence of the rs144204026 SNP.

As a result of sequencing, the patient is determined to have one copy the SMAD7 gene rs144204026 polymorphism (i.e., an "A" at the position) and one copy of the consensus sequence (i.e., a "G" at the position). Based on this determination, the patient is administered two different antisense therapeutics, one having the sequence of Mongersen (i.e., SEQ ID NO:5) and one having the sequence of Mongersen in which the nucleotide that corresponds to the rs144204026 polymorphism has been substituted (i.e., SEQ ID NO:11).

Following treatment using the combination of antisense therapeutics, the patient experiences reduction in symptoms associated with Crohn's disease.

Example 2—a Patient Homozygous for the rs144204026 SNP

A patient is diagnosed with Crohn's disease. Prior to beginning therapy, the patient's SMAD7 gene sequence is analyzed in the patient using standard sequencing techniques to determine the presence or absence of the rs144204026 SNP.

As a result of sequencing, the patient is determined to have two copies the SMAD7 gene rs144204026 polymorphism (i.e., an "A" at the position). Based on this determination, the patient is administered a single antisense therapeutic having the sequence of Mongersen in which the nucleotide that corresponds to the rs144204026 polymorphism has been substituted (e.g., SEQ ID NO:11).

Following treatment using the antisense therapeutic, the patient experiences reduction in symptoms associated with Crohn's disease.

SEQUENCES

SEQ ID NO:1 (Coding Sequence CDS (288-1568) of NM_005904.3; *Homo sapiens* SMAD family member 7 (SMAD7), transcript variant 1, mRNA)—Target sequence of Mongersen target and its derivatives underlined (108-128); SNP (g/a) double underlined;

```
ATG TTCAGGACCA AACGATCTGC GCTCGTCCGG CGTCTCTGGA GGAGCCGTGC

GCCCGGCGGC GAGGACGAGG AGGAGGGCGC AGGGGGAGGT GGAGGAGGAG

GCGAGCTGCG GGGAGAAGGG GCGACGGACA GCCGAGCGCA TGGGGCCGGT

GGCGGCGGCC CGGGCAGGGC TGGATGCTGC CTGGGCAAGG CGGTGCGAGG

TGCCAAAGGT CACCACCATC CCCACCCGCC AGCCGCGGGC GCCGGCGCGG

CCGGGGGCGC CGAGGCGGAT CTGAAGGCGC TCACGCACTC GGTGCTCAAG

AAACTGAAGG AGCGGCAGCT GGAGCTGCTG CTCCAGGCCG TGGAGTCCCG

CGGCGGGACG CGCACCGCGT GCCTCCTGCT GCCCGGCCGC CTGGACTGCA

GGCTGGGCCC GGGGGCGCCC GCCGGCGCGC AGCCTGCGCA GCCGCCCTCG

TCCTACTCGC TCCCCCTCCT GCTGTGCAAA GTGTTCAGGT GGCCGGATCT

CAGGCATTCC TCGGAAGTCA AGAGGCTGTG TTGCTGTGAA TCTTACGGGA

AGATCAACCC CGAGCTGGTG TGCTGCAACC CCCATCACCT TAGCCGACTC

TGCGAACTAG AGTCTCCCCC CCCTCCTTAC TCCAGATACC CGATGGATTT

TCTCAAACCA ACTGCAGACT GTCCAGATGC TGTGCCTTCC TCCGCTGAAA

CAGGGGAAC GAATTATCTG GCCCCTGGGG GGCTTTCAGA TTCCCAACTT

CTTCTGGAGC CTGGGGATCG GTCACACTGG TGCGTGGTGG CATACTGGGA

GGAGAAGACG AGAGTGGGGA GGCTCTACTG TGTCCAGGAG CCCTCTCTGG

ATATCTTCTA TGATCTACCT CAGGGGAATG GCTTTTGCCT CGGACAGCTC

AATTCGGACA ACAAGAGTCA GCTGGTGCAG AAGGTGCGGA GCAAAATCGG

CTGCGGCATC CAGCTGACGC GGGAGGTGGA TGGTGTGTGG GTGTACAACC
```

-continued
```
GCAGCAGTTA CCCCATCTTC ATCAAGTCCG CCACACTGGA CAACCCGGAC

TCCAGGACGC TGTTGGTACA CAAGGTGTTC CCCGGTTTCT CCATCAAGGC

TTTCGACTAC GAGAAGGCGT ACAGCCTGCA GCGGCCCAAT GACCACGAGT

TTATGCAGCA GCCGTGGACG GGCTTTACCG TGCAGATCAG CTTTGTGAAG

GGCTGGGGCC AGTGCTACAC CCGCCAGTTC ATCAGCAGCT GCCCGTGCTG

GCTAGAGGTC ATCTTCAACA GCCGGTAG
```

SEQ ID NO:2 (truncated Mongersen target-sequence; SNP rs144204026 location highlighted)

```
5'-CTGCGGGGAGAAGGGGCGAC-3'
```

SEQ ID NO:3 (Mongersen target-sequence; SNP rs144204026 location highlighted)

```
5'-GCTGCGGGAGAAGGGGCGAC-3'
```

SEQ ID NO:4 (truncated Mongersen sequence; the highlighted position corresponds to the location of SNP rs144204026)

```
5'-GTCGCCCCTTCTCCCGCAG-3'
```

SEQ ID NO:5 (Mongersen sequence; the highlighted position corresponds to the location of SNP rs144204026)

```
5'-GTCGCCCCTTCTCCCGCAGC-3'
```

SEQ ID NO:6 (truncated Mongersen; the highlighted position corresponds to the location of SNP rs144204026)

```
5'-GTXGCCCCTTCTCCXGCAG-3'
```

X is 5-methyl-2'-deoxycytidine and wherein all internucleotide linkages are phosphorothioate linkages
SEQ ID NO:7 (Mongersen; the highlighted position corresponds to the location of SNP rs144204026)

```
5'-GTXGCCCCTTCTCCCXGCAGC-3'
```

X is 5-methyl-2'-deoxycytidine and wherein all internucleotide linkages are phosphorothioate linkages
SEQ ID NO:8 (polymorphic variant of truncated Mongersen target-sequence; SNP rs144204026 position highlighted)

```
5'-CTGCGGAGAGAAGGGGCGAC-3'
```

SEQ ID NO:9 (polymorphic variant of Mongersen target-sequence; SNP rs144204026 position highlighted)

```
5'-GCTGCGGAGAGAAGGGGCGAC-3'
```

SEQ ID NO:10 (polymorphic variant of truncated Mongersen sequence; position targeting SNP rs144204026 highlighted)

```
5'-GTCGCCCCTTCTCTCCGCAG-3'
```

SEQ ID NO:11 (polymorphic variant of Mongersen sequence; position targeting SNP rs144204026 highlighted)

```
5'-GTCGCCCCTTCTCTCCGCAGC-3'
```

SEQ ID NO:12 (polymorphic variant of truncated Mongersen; position targeting SNP rs144204026 highlighted)

```
5'-GTXGCCCCTTCTCTCXGCAG-3'
```

X is 5-methyl-2'-deoxycytidine and wherein all internucleotide linkages are phosphorothioate linkages
SEQ ID NO:13 (polymorphic variant of Mongersen; position targeting SNP rs144204026 highlighted)

```
5'-GTXGCCCCTTCTCTCXGCAGC-3'
```

X is 5-methyl-2'-deoxycytidine and wherein all internucleotide linkages are phosphorothioate linkages
SEQ ID NO:14 (variant of Mongersen; the highlighted position corresponds to the location of SNP rs144204026)

```
5'-ZTXGCCCCTTCTCCCXGCAZC-3'
```

X is 5-methyl 2'-deoxycytidine and Z is 2'-deoxyguanosine methylphosphonate
SEQ ID NO:15 (variant of truncated Mongersen; the highlighted position corresponds to the location of SNP rs144204026)

```
5'-ZTXGCCCCTTCTCCCXGCAZ-3'
```

X is 5-methyl 2'-deoxycytidine and Z is 2'-deoxyguanosine methylphosphonate
SEQ ID NO:16 (variant of Mongersen; the highlighted position corresponds to the location of SNP rs144204026)

```
5'-GTXGCCCCTTCTCCCXGCAGC-3'
```

X is 5-methyl 2'-deoxycytidine
SEQ ID NO:17 (variant of Mongersen; the highlighted position corresponds to the location of SNP rs144204026)

```
5'-GTXYCCCCTTCTCCCXYCAGC-3'
```

X is a nucleotide comprising a nitrogenous base selected from the group consisting of cytosine and 5-methylcytosine or a 2'-O-methylcytosine nucleotide, and Y is a nucleotide comprising a nitrogenous base selected from the group consisting of guanine and 5-methylguanine or a 2'-O-methylguanine nucleotide, provided that at least one of the nucleotides X or Y comprises a methylated nitrogenous base SEQ ID NO:18 (polymorphic variant of truncated Mongersen variant; position targeting SNP rs144204026 highlighted)

5'-ZTXGCCCCTTCTCTCXGCAZ-3',

X is 5-methyl 2'-deoxycytidine and Z is 2'-deoxyguanosine methylphosphonate
SEQ ID NO:19 (polymorphic variant of Mongersen variant; position targeting SNP rs144204026 highlighted)

5'-ZTXGCCCCTTCTCTCXGCAZC-3'

X is 5-methyl 2'-deoxycytidine and Z is 2'-deoxyguanosine methylphosphonate
SEQ ID NO:20 (polymorphic variant of Mongersen variant; position targeting SNP rs144204026 highlighted)

5'-GTXGCCCCTTCTCTCXGCAGC-3'

X is 5-methyl 2'-deoxycytidine
SEQ ID NO:21 (polymorphic variant of Mongersen variant; position targeting SNP rs144204026 highlighted)

5'-GTXYCCCCTTCTCTCXYCAGC-3'

X is a nucleotide comprising a nitrogenous base selected from the group consisting of cytosine and 5-methylcytosine or a 2'-O-methylcytosine nucleotide, and Y is a nucleotide comprising a nitrogenous base selected from the group consisting of guanine and 5-methylguanine or a 2'-O-methylguanine nucleotide, provided that at least one of the nucleotides X or Y comprises a methylated nitrogenous base.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

INCORPORATION BY REFERENCE

The entire contents of all patents, published patent applications, websites, and other references cited herein are hereby expressly incorporated herein in their entireties by reference.

The invention claimed is:

1. A SMAD7 antisense oligonucleotide comprising the nucleotide sequence of SEQ ID NO:11 (5'-GTCGCCCCT-TCTCTCCGCAGC-3'), wherein at least one internucleotide linkage is a phosphorothioate linkage.

2. A SMAD7 antisense oligonucleotide comprising the nucleotide sequence of SEQ ID NO:13 (5'-GTXGCCCCT-TCTCTCXGCAGC-3'), wherein X is a nucleotide comprising 5-methyl-2'-deoxycytidine and wherein all internucleotide linkages are phosphorothioate linkages.

3. A SMAD7 antisense oligonucleotide comprising the nucleotide sequence of SEQ ID NO:13 (5'-GTXGCCCCT-TCTCTCXGCAGC-3'), wherein X is a nucleotide comprising 5-methyl-2'-deoxycytidine, or a complement thereof.

4. The SMAD7 antisense oligonucleotide of claim 3, wherein at least one internucleotide linkage is a phosphorothioate linkage.

5. The SMAD7 antisense oligonucleotide of claim 3, wherein the 2'-deoxyribonucleotides are replaced by corresponding ribonucleotides.

6. A pharmaceutical composition comprising the SMAD7 antisense oligonucleotide of claim 3 and a pharmaceutically acceptable adjuvant and/or excipient.

7. The pharmaceutical composition of claim 6, wherein the pharmaceutical composition is an oral pharmaceutical composition.

8. The SMAD7 antisense oligonucleotide of claim 1, wherein all internucleotide linkages are phosphorothioate linkages.

* * * * *

SEQUENCE LISTING

```
<160> NUMBER OF SEQ ID NOS: 21

<210> SEQ ID NO 1
<211> LENGTH: 1281
<212> TYPE: DNA
<213> ORGANISM: Homo sapiens

<400> SEQUENCE: 1
atgttcagga ccaaacgatc tgcgctcgtc cggcgtctct ggaggagccg tgcgcccggc     60
ggcgaggacg aggaggaggg cgcaggggga ggtggaggag gaggcgagct gcggggagaa    120
ggggcgacgg acagccgagc gcatggggcc ggtggcggcg gcccgggcag ggctggatgc    180
tgcctgggca aggcggtgcg aggtgccaaa ggtcaccacc atccccaccc gccagccgcg    240
ggcgccggcg cggccggggg cgccgaggcg gatctgaagg cgctcacgca ctcggtgctc    300
aagaaactga aggagcggca gctggagctg ctgctccagg ccgtggagtc ccgcggcggg    360
acgcgcaccg cgtgcctcct gctgcccggc cgcctggact gcaggctggg cccgggggcg    420
cccgccggcg cgcagcctgc gcagccgccc tcgtcctact cgctcccccct cctgctgtgc    480 aaagtgttca ggtggccgga tctcaggcat tcctcggaag tcaagaggct gtgttgctgt    540
gaatcttacg ggaagatcaa ccccgagctg gtgtgctgca accccatca ccttagccga    600 ctctgcgaac tagagtctcc ccccctcct tactccagat acccgatgga ttttctcaaa    660
ccaactgcag actgtccaga tgctgtgcct tcctccgctg aaacaggggg aacgaattat    720
ctggcccctg gggggctttc agattcccaa cttcttctgg agcctgggga tcggtcacac    780
tggtgcgtgg tggcatactg ggaggagaag acgagagtgg ggaggctcta ctgtgtccag    840
gagccctctc tggatatctt ctatgatcta cctcagggga atggcttttg cctcggacag    900
```

```
ctcaattcgg acaacaagag tcagctggtg cagaaggtgc ggagcaaaat cggctgcggc      960
atccagctga cgcgggaggt ggatggtgtg tgggtgtaca accgcagcag ttaccccatc     1020
ttcatcaagt ccgccacact ggacaacccg gactccagga cgctgttggt acacaaggtg     1080
ttccccggtt tctccatcaa ggctttcgac tacgagaagg cgtacagcct gcagcggccc     1140
aatgaccacg agtttatgca gcagccgtgg acgggcttta ccgtgcagat cagctttgtg     1200
aagggctggg gccagtgcta cacccgccag ttcatcagca gctgcccgtg ctggctagag     1260
gtcatcttca acagccggta g                                               1281
```

```
<210> SEQ ID NO 2
<211> LENGTH: 20
<212> TYPE: DNA
<213> ORGANISM: Homo sapiens

<400> SEQUENCE: 2
ctgcggggag aagggcgac                                                    20

<210> SEQ ID NO 3
<211> LENGTH: 21
<212> TYPE: DNA
<213> ORGANISM: Homo sapiens

<400> SEQUENCE: 3
gctgcgggga agggggcga c                                                  21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gtcgcccctt ctccccgcag                                                   20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtcgcccctt ctccccgcag c                                                 21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-methyl-2'-deoxycytidine
<220> FEATURE:
<221> NAME/KEY: modified_base
<222> LOCATION: (16)..(16)
<223> OTHER INFORMATION: 5-methyl-2'-deoxycytidine

<400> SEQUENCE: 6
```
gtcgcccctt ctccccgcag                                                    20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-methyl-2'-deoxycytidine
<220> FEATURE:
<221> NAME/KEY: modified_base
<222> LOCATION: (16)..(16)
<223> OTHER INFORMATION: 5-methyl-2'-deoxycytidine

<400> SEQUENCE: 7
gtcgcccctt ctccccgcag c                                                  21

<210> SEQ ID NO 8
<211> LENGTH: 20
<212> TYPE: DNA
<213> ORGANISM: Homo sapiens

<400> SEQUENCE: 8
ctgcggagag aagggggcgac                                                   20

<210> SEQ ID NO 9
<211> LENGTH: 21
<212> TYPE: DNA
<213> ORGANISM: Homo sapiens

<400> SEQUENCE: 9
gctgcggaga gaaggggcga c                                                  21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gtcgcccctt ctctccgcag                                                    20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtcgcccctt ctctccgcag c                                                  21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (3)..(3)
<223> OTHER INFORMATION: 5-methyl-2'-deoxycytidine
<220> FEATURE:
<221> NAME/KEY: modified_base
<222> LOCATION: (16)..(16)
<223> OTHER INFORMATION: 5-methyl-2'-deoxycytidine

<400> SEQUENCE: 12 gtcgccccttctctccgcag                                              20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-methyl-2'-deoxycytidine
<220> FEATURE:
<221> NAME/KEY: modified_base
<222> LOCATION: (16)..(16)
<223> OTHER INFORMATION: 5-methyl-2'-deoxycytidine

<400> SEQUENCE: 13 gtcgccccttctctccgcagc                                             21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxyguanosine methylphosphonate
<220> FEATURE:
<221> NAME/KEY: modified_base
<222> LOCATION: (3)..(3)
<223> OTHER INFORMATION: 5-methyl-2'-deoxycytidine
<220> FEATURE:
<221> NAME/KEY: modified_base
<222> LOCATION: (16)..(16)
<223> OTHER INFORMATION: 5-methyl-2'-deoxycytidine
<220> FEATURE:
<221> NAME/KEY: modified_base
<222> LOCATION: (20)..(20)
<223> OTHER INFORMATION: 2'-deoxyguanosine methylphosphonate

<400> SEQUENCE: 14 gtcgccccttctccccgcagc                                             21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxyguanosine methylphosphonate
<220> FEATURE:
<221> NAME/KEY: modified_base
<222> LOCATION: (3)..(3)
<223> OTHER INFORMATION: 5-methyl-2'-deoxycytidine
<220> FEATURE:
<221> NAME/KEY: modified_base
```

```
<222> LOCATION: (16)..(16)
<223> OTHER INFORMATION: 5-methyl-2'-deoxycytidine
<220> FEATURE:
<221> NAME/KEY: modified_base
<222> LOCATION: (20)..(20)
<223> OTHER INFORMATION: 2'-deoxyguanosine methylphosphonate

<400> SEQUENCE: 15
gtcgcccctt ctccccgcag                                              20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-methyl-2'-deoxycytidine
<220> FEATURE:
<221> NAME/KEY: modified_base
<222> LOCATION: (16)..(16)
<223> OTHER INFORMATION: 5-methyl-2'-deoxycytidine

<400> SEQUENCE: 16
gtcgcccctt ctccccgcag c                                            21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: Cytosine, 5-methylcytosine or a 2'-O-
      methylcytosine nucleotide
<220> FEATURE:
<221> NAME/KEY: modified_base
<222> LOCATION: (4)..(4)
<223> OTHER INFORMATION: Guanine, 5-methylguanine or a 2'-O-
      methylguanine nucleotide
<220> FEATURE:
<221> NAME/KEY: modified_base
<222> LOCATION: (16)..(16)
<223> OTHER INFORMATION: Cytosine, 5-methylcytosine or a 2'-O-
      methylcytosine nucleotide
<220> FEATURE:
<221> NAME/KEY: modified_base
<222> LOCATION: (17)..(17)
<223> OTHER INFORMATION: Guanine, 5-methylguanine or a 2'-O-
      methylguanine nucleotide
<220> FEATURE:
<223> OTHER INFORMATION: See specification as filed for detailed
      description of substitutions and preferred embodiments

<400> SEQUENCE: 17
gtcgcccctt ctccccgcag c                                            21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
```

<223> OTHER INFORMATION: 2'-deoxyguanosine methylphosphonate
<220> FEATURE:
<221> NAME/KEY: modified_base
<222> LOCATION: (3)..(3)
<223> OTHER INFORMATION: 5-methyl-2'-deoxycytidine
<220> FEATURE:
<221> NAME/KEY: modified_base
<222> LOCATION: (16)..(16)
<223> OTHER INFORMATION: 5-methyl-2'-deoxycytidine
<220> FEATURE:
<221> NAME/KEY: modified_base
<222> LOCATION: (20)..(20)
<223> OTHER INFORMATION: 2'-deoxyguanosine methylphosphonate

<400> SEQUENCE: 18
gtcgcccctt ctctccgcag                                           20

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxyguanosine methylphosphonate
<220> FEATURE:
<221> NAME/KEY: modified_base
<222> LOCATION: (3)..(3)
<223> OTHER INFORMATION: 5-methyl-2'-deoxycytidine
<220> FEATURE:
<221> NAME/KEY: modified_base
<222> LOCATION: (16)..(16)
<223> OTHER INFORMATION: 5-methyl-2'-deoxycytidine
<220> FEATURE:
<221> NAME/KEY: modified_base
<222> LOCATION: (20)..(20)
<223> OTHER INFORMATION: 2'-deoxyguanosine methylphosphonate

<400> SEQUENCE: 19
gtcgcccctt ctctccgcag c                                         21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-methyl-2'-deoxycytidine
<220> FEATURE:
<221> NAME/KEY: modified_base
<222> LOCATION: (16)..(16)
<223> OTHER INFORMATION: 5-methyl-2'-deoxycytidine

<400> SEQUENCE: 20
gtcgcccctt ctctccgcag c                                         21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)

```
<223> OTHER INFORMATION: Cytosine, 5-methylcytosine or a 2'-O-
      methylcytosine nucleotide
<220> FEATURE:
<221> NAME/KEY: modified_base
<222> LOCATION: (4)..(4)
<223> OTHER INFORMATION: Guanine, 5-methylguanine or a 2'-O-
      methylguanine nucleotide
<220> FEATURE:
<221> NAME/KEY: modified_base
<222> LOCATION: (16)..(16)
<223> OTHER INFORMATION: Cytosine, 5-methylcytosine or a 2'-O-
      methylcytosine nucleotide
<220> FEATURE:
<221> NAME/KEY: modified_base
<222> LOCATION: (17)..(17)
<223> OTHER INFORMATION: Guanine, 5-methylguanine or a 2'-O-
      methylguanine nucleotide
<220> FEATURE:
<223> OTHER INFORMATION: See specification as filed for detailed
      description of substitutions and preferred embodiments

<400> SEQUENCE: 21
gtcgccsctt ctctccgcag c                                           21
```